United States Patent [19]

Aya et al.

[11] 4,441,913

[45] Apr. 10, 1984

[54] SUBSTITUTED PHENOXYPROPIONATES AND HERBICIDAL COMPOSITIONS

[75] Inventors: Masahiro Aya, Kodaira; Junichi Saito, Mitaka; Kazuomi Yasui, Tokyo; Kozo Shiokawa, Kawasaki; Koichi Moriya, Hachioji, all of Japan

[73] Assignee: Nihon Tokushu Noyaku Seizo K.K., Tokyo, Japan

[21] Appl. No.: 389,525

[22] Filed: Jun. 17, 1982

[30] Foreign Application Priority Data

Jun. 25, 1981 [JP] Japan .................................. 56-97486
Sep. 16, 1981 [JP] Japan .................................. 56-144778
Dec. 7, 1981 [JP] Japan .................................. 56-195604
Dec. 7, 1981 [JP] Japan .................................. 56-195605

[51] Int. Cl.³ .................... C07D 213/64; A01N 43/40
[52] U.S. Cl. ........................................ 71/94; 546/297;
546/300; 546/301; 546/302; 560/21; 560/22; 560/61; 560/62
[58] Field of Search ............... 546/297, 300, 301, 302; 71/94

[56] References Cited

FOREIGN PATENT DOCUMENTS 2909816 9/1979 Fed. Rep. of Germany .
2360253 3/1978 France .

*Primary Examiner*—Alan L. Rotman
*Attorney, Agent, or Firm*—Sprung, Horn, Kramer & Wood

[57] ABSTRACT

Novel substituted phenoxypropionates of the formula

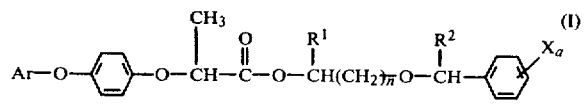

in which
$R^1$ and $R^2$ each independently are a hydrogen atom or a $C_1$ to $C_6$ alkyl group,
X is a hydrogen or halogen atom, nitro, $C_1$ to $C_6$ alkyl or $C_1$ to $C_6$ alkoxy,
a and n each independently are 1 or 2, and
Ar is a group of the formula

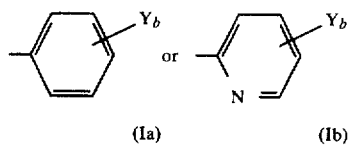

wherein
Y is a trifluoromethyl group, a halogen atom or a nitro, cyano or $C_1$ to $C_6$ alkyl group, and
b is 1, 2 or 3, and their use as herbicides.

Novel intermediates of the formulae

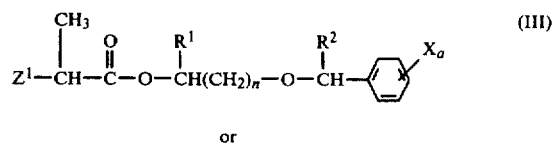

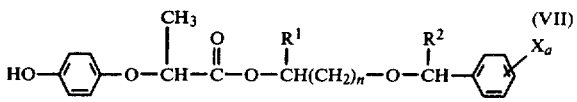

in which formulae
$R^1$, $R^2$, X, a and n have the meanings given above and $Z^1$ represents halogen.

21 Claims, No Drawings

SUBSTITUTED PHENOXYPROPIONATES AND HERBICIDAL COMPOSITIONS

The present invention relates to certain novel substituted phenoxypropionates, to herbicidal compositions containing them and to methods of combating weeds utilizing such compounds.

The present invention also relates to novel intermediates for the preparation of said substituted phenoxypropionates.

It has been disclosed in U.S. Pat. No. 4,046,553 corresponding to Japanese Laid-Open Patent Application No. 51-106,735 that herbicidal activity is possessed by compounds of the general formula $$X^1\text{-pyridyl-}X^2\text{-O-phenyl-O-CH(Y)-C(=O)-Z-H}$$

wherein
$X^1$ and $X^2$ each represents halogen,
Y represents hydrogen or alkyl having 6 or less carbon atoms, and
Z represents oxygen or sulfur,
and the salts, esters, amides, and halides thereof.

It has been disclosed in Japanese Laid-open Patent Application No. 52-131,545 corresponding to DE-OS (German published specification) No. 2,617,804 that herbicidal activity is possessed by compounds of the general formula $$CF_3\text{-phenyl(R)-O-phenyl-O-CH(CH}_3\text{)-C(=O)-O-R}_1$$

wherein
R represents hydrogen or halogen,
$R_1$ represents:
(a) straight- or branched chain $(C_1-C_{12})$alkyl (which is substituted by cyclohexyl, halophenyl, nitrophenyl, $(C_1-C_6)$alkylphenyl, phenoxy (which is mono- to tri-substituted in some cases with halogen and/or $(C_1-C_4)$alkyl), $(C_5-C_6)$alkoxy, $(C_5-C_6)$-alkoxy-$(C_2-C_4)$alkoxy, $(C_1-C_4)$alkoxyethoxyethoxy, $(C_1-C_4)$acyl, a group represented by the general formula $$-N\begin{matrix}R_2\\R_3\end{matrix} \text{ or } \left[\begin{matrix}R_2\\|\\N-R_3\\|\\R_4\end{matrix}\right]^+ Z^-,$$

or, in the 2 position or a position remote from the carboxyl, mono- or poly-substituted by phenyl);
(b) cyclohexenyl or phenyl-$(C_3-C_4)$alkenyl;
(c) $(C_3-C_4)$alkynyl (which is optionally mono- or di-substituted by straight or branched chain $(C_1-C_4)$alkyl, halogen, phenyl, halophenyl or $(C_1-C_4)$alkylphenyl), provided that $R_1$ does not represent unsubstituted propargyl or butynyl;

(d) one of the groups represented by the following general formulae:

$$-R_1'\text{-CH}\begin{matrix}CH_3\\|\\O\\|\end{matrix}\begin{matrix}CH_3\\|\\O\\|\end{matrix}\text{-CH}_2, \quad -R_1'\text{-O-CO-R}_5,$$

(IV')         (V')

$$-R_1'\text{-O-CO-N}\begin{matrix}R_6\\R_5\end{matrix} \text{ and } -R_1'\text{-S(O)}_n\text{-R}_6$$

(VI')         (VII')

or
(e) $(C_1-C_2)$alkyl substituted by furyl, tetrahydrofuryl, pyridyl or oxiranyl,
$R_2$ represents hydrogen, $(C_1-C_4)$alkyl or $(C_1-C_4)$alkoxy,
$R_3$ represents hydrogen, $(C_1-C_4)$alkyl or phenyl, or
$R_2$ and $R_3$ together form 4- or 5-membered, saturated or unsaturated alkylene chain one methylene of which may optionally be replaced by —O—, $$-\underset{\underset{O}{\|}}{C}-$$

or —N—$(C_1-C_4)$—alkyl,
$R_4$ represents hydrogen or $(C_1-C_4)$alkyl,
Z represents an inorganic or organic anion,
$R_1'$ represents straight or branched chain $(C_1-C_{12})$alkylene,
$R_5$ represents hydrogen, $(C_1-C_4)$alkyl, $(C_1-C_4)$haloalkyl, phenyl optionally substituted by halogen, nitro and/or $(C_1-C_4)$alkyl, or group represented by the formula $$-\underset{\underset{CH_3}{|}}{CH}-O-\text{phenyl-O-phenyl-}CF_3 \quad (VIII')$$

or $$-\underset{\underset{CH_3}{|}}{CH}-O-\text{phenyl-O-phenyl(Cl)-}Cl \quad (IX')$$

$R_6$ represents $(C_1-C_4)$alkyl, and
n is 0, 1 or 2.

It has been disclosed in Japanese Laid-open Patent Application No. 52-144,637 corresponding to DE-OS (German published specification) No. 2,623,558 that herbicidal activity is possessed by compounds of the general formula $$(R)_n\text{-phenyl-O-phenyl-O-CH(CH}_3\text{)-C(=O)-Y-R}_1$$

wherein each R represents the same or different group selected from halogen, (C$_1$–C$_4$)alkyl, and (C$_1$–C$_4$)alkoxy,
Y represents O or S,
n is 1 or 2,
R$_1$ represents:
(a) straight or branched chain (C$_1$–C$_{12}$)alkyl (which is substituted by cyclohexyl, halophenyl, nitrophenyl, (C$_1$–C$_4$)alkylphenyl, or a group represented by the general formula

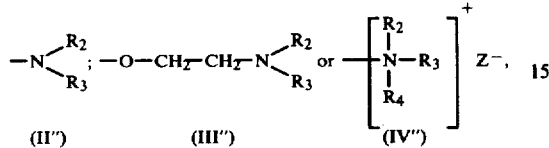

(II'')   (III'')   (IV'')

or mono- or poly-substituted by the same or different group selected from hydroxy, halogen, rhodanide, and phenyl, in 2- or more distant position from Y);
(b) mono- or di-(C$_1$–C$_4$)alkylcyclohexyl;
(c) cyclohexenyl or (C$_3$–C$_4$)alkenyl (which may be substituted by halogen, hydroxy, phenyl, halophenyl or (C$_1$–C$_4$)alkylphenyl);
(d) naphthyl or phenyl (which is in some cases mono- or poly-substituted by (C$_1$–C$_4$)alkyl, (C$_1$–C$_3$)haloalkyl, CF$_3$, NO$_2$, CN, SCN, CHO, (C$_1$–C$_3$)alkoxy, (C$_1$–C$_3$)alkoxycarbonyl, aminocarbonyl, di-(C$_1$–C$_4$)alkylamino, or (C$_1$–C$_2$)alkylthio, and which may further contain halogen), or when Y is O, R$_1$ also represents:
(e) straight or branched chain (C$_3$–C$_6$)alkynyl (which is in some cases mono- or poly-substituted by (C$_1$–C$_4$)alkyl, (C$_1$–C$_4$)alkoxy, halogen, phenyl, halophenyl, or (C$_1$–C$_4$)alkylphenyl);
(f) halocyclohexyl optionally substituted by (C$_1$–C$_4$)alkyl;
(g) group represented by the formula of

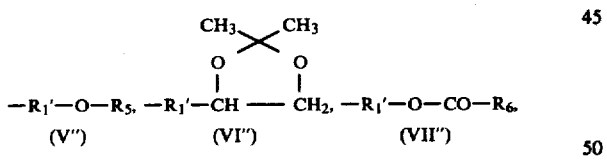

(V'')   (VI'')   (VII'')

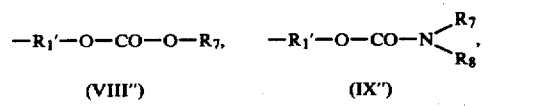

(VIII'')   (IX'')

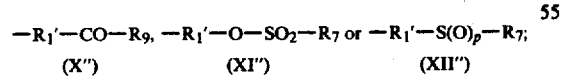

(X'')   (XI'')   (XII'')

(h) (C$_1$–C$_2$)alkyl substituted by a furyl, tetrahydrofuryl, pyridyl or by oxiranyl;
(i) (C$_2$–C$_4$)alkyl substituted by 3 to 7 chlorine and/or fluorine, or, when Y is S, R$_1$ represents:
(k) (C$_3$–C$_4$)alkenyl,
R$_2$ represents hydrogen, (C$_1$–C$_4$)alkyl, (C$_1$–C$_4$)alkoxy, hydroxyethyl or chloroethyl,
R$_3$ represents hydrogen, (C$_1$–C$_4$)alkyl, chloroethyl, phenyl, halophenyl, (C$_1$–C$_4$)alkylphenyl, hydroxyethyl or aliphatic (C$_1$–C$_4$)acyl, or, when taken together,
R$_2$ and R$_3$ represents 2-, 4- or 5-membered, saturated or unsaturated hydrocarbon chain one, carbon atom of which may be replaced by —O—, —CO—, —N—, —NH— or —N—(C$_1$–C$_4$)alkyl,
R$_4$ represents hydrogen or (C$_1$–C$_4$)alkyl,
Z represents an inorganic or organic acid anion, R$_1$' represents a straight chain or branched chain (C$_1$–C$_{12}$)alkylene,
R$_5$ represents (C$_1$–C$_6$)alkyl, (C$_1$–C$_4$)haloalkyl, (C$_2$–C$_8$)alkoxyalkyl, (C$_3$–C$_{12}$)alkoxyalkoxy, hydroxyethyl or phenyl optionally mono- or di-substituted by halogen and/or (C$_1$–C$_3$)alkyl,
R$_6$ represents hydrogen, (C$_1$–C$_4$)alkyl, (C$_1$–C$_4$)haloalkyl, phenyl optionally substituted by halogen, nitro and/or (C$_1$–C$_4$)alkyl, or a group of the general formula

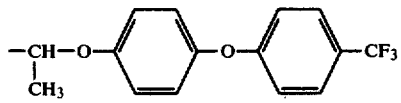

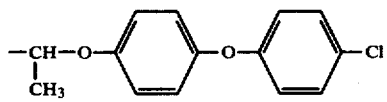

or

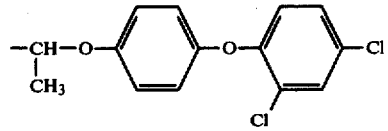

R$_7$ represents (C$_1$–C$_4$)alkyl, phenyl, halophenyl, nitrophenyl or (C$_1$–C$_4$)alkylphenyl,
R$_8$ represents hydrogen, (C$_1$–C$_4$)alkyl or (C$_1$–C$_4$)alkoxy,
R$_9$ represents (C$_1$–C$_4$)alkyl, and
p is 0, 1 or 2.

It has further been disclosed in DE-OS (German published specification) No. 2,812,571, corresponding to Japanese Laid-open Patent Application No. 54-119,476, that herbicidal activity is possessed by compounds of the general formula

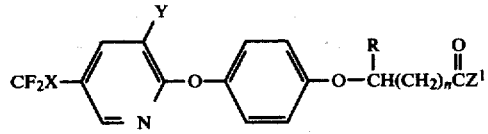

wherein
X represents fluorine or chlorine,
Y represents hydrogen or chlorine,
R represents hydrogen, methyl or ethyl,
n is 0 or 2,
Z$^1$ represents hydroxy, (C$_1$–C$_6$)alkoxy whose alkyl moiety is optionally substituted by 1 to 3 halogen, (C$_1$–C$_4$)alkoxy-(C$_1$–C$_4$)alkoxy, (C$_2$–C$_4$)alkenyloxy, (C$_2$–C$_4$)alkynyloxy, (C$_3$–C$_6$)cycloalkyl whose cycloalkyl moiety is optionally substituted by (C$_1$–C$_4$)alkyl, (C$_1$–C$_4$)alkoxycarbonyl-(C$_1$–C$_4$)alkoxy, phenoxy whose phenyl moiety is optionally substituted by 1 to 3 halogen or ($C_1$-$C_4$)alkyl, benzyloxy, glycidyloxy, ($C_1$-$C_4$)alkylthio, ($C_2$-$C_4$)alkenylthio, phenylthio whose phenyl moiety is optionally substituted by 1 to 3 halogen or ($C_1$-$C_4$)alkyl, amino, ($C_1$-$C_4$)-alkylamino, ($C_1$-$C_4$)alkoxycarbonylmethylamino, hydroxycarbonylmethylamino, anilino group whose phenyl moiety may optionally be substituted by 1 to 3 halogen, pyridin-2-ylamino, an —O— cation, or halogen.

The present invention now provides, as new compounds, the substituted phenoxypropionates of the general formula $$Ar-O-\underset{}{\bigcirc}-O-\underset{CH_3}{\underset{|}{CH}}-\underset{O}{\overset{\|}{C}}-O-\underset{R^1}{\underset{|}{CH}}(CH_2)_n-O-\underset{R^2}{\underset{|}{CH}}-\bigcirc X_a \quad (I)$$

in which
  $R^1$ and $R^2$ each independently represent a hydrogen atom or a $C_1$ to $C_6$ alkyl group,
  X represents a hydrogen or halogen atom or a nitro, $C_1$ to $C_6$ alkyl or $C_1$ to $C_6$ alkoxy group,
  a and n each independently are 1 or 2, and
  Ar represents a group of the general formula $$-\bigcirc-Y_b \quad \text{or} \quad -\underset{N}{\bigcirc}-Y_b$$

(Ia)  (Ib)

wherein
  Y represents a trifluoromethyl group, a halogen atom or a nitro, cyano or $C_1$ to $C_6$ alkyl group, and
  b is 1, 2 or 3.

The invention also provides a process for the preparation of a substituted phenoxypropionate of the formula (I), in which process (a) a compound of the general formula $$Ar-O-\bigcirc-OM \quad (II)$$

in which
  Ar has the meaning given above, and
  M represents a hydrogen atom or an alkali metal atom,
is reacted with a compound of the general formula $$Z^1-\underset{CH_3}{\underset{|}{CH}}-\underset{O}{\overset{\|}{C}}-O-\underset{R^1}{\underset{|}{CH}}(CH_2)_n-O-\underset{R^2}{\underset{|}{CH}}-\bigcirc X_a \quad (III)$$

in which
  $R^1$, $R^2$, X, a and n have the meanings given above, and
  $Z^1$ represents a halogen atom, or (b) a compound of the general formula $$Ar-O-\bigcirc-O-\underset{CH_3}{\underset{|}{CH}}-\underset{O}{\overset{\|}{C}}-Z^2 \quad (IV)$$

in which
  Ar has the meaning given above, and
  $Z^2$ represents a hydroxyl group or a halogen atom,
is reacted with a compound of the general formula $$HO-\underset{R^1}{\underset{|}{CH}}(CH_2)_n-O-\underset{R^2}{\underset{|}{CH}}-\bigcirc X_a \quad (V)$$

in which
  $R^1$, $R^2$, X, a and n have the meanings given above, or (c) a compound of the general formula $$Ar-Z^1 \quad (VI)$$

in which Ar and $Z^1$ have the meanings given above, is reacted with a compound of the general formula $$MO-\bigcirc-O\underset{CH_3}{\underset{|}{CH}}-\underset{O}{\overset{\|}{C}}-O-\underset{R^1}{\underset{|}{CH}}(CH_2)_n-O-\underset{R^2}{\underset{|}{CH}}-\bigcirc X_a \quad (VII)$$

in which $R^1$, $R^2$, X, M, a and n have the meanings given above.

Surprisingly the substituted phenoxypropionate compounds of the present invention, which have not previously been described in the literature, can be synthesized with ease in high yield, and are novel active compounds showing selective excellent herbicidal activity against gramineous weeds without causing substantial phytotoxicity on agricultural crops. It is particularly surprising that the compounds of the present invention show excellent properties which are not shown by structurally similar prior art compounds, in particular that, coupled with good toleration by useful plants, they show sufficient herbicidal activity in low amounts, and that they control regeneration of weeds, especially perennial gramineous weeds, over a long period of time due to their excellent lasting effect.

Preferred compounds according to the present invention, and corresponding starting materials are those in which Ar represents a group of formula (Ia) or (Ib), in which
  Y represents a trifluoromethyl group, a fluorine, chlorine, bromine or iodine atom or a nitro, cyano, methyl, ethyl, propyl, isopropyl, n-, iso-, sec- or tert-butyl group,
  b is 1, 2 or 3,
  $R^1$ and $R^2$ each independently represent a hydrogen atom or a methyl, ethyl, n-propyl, isopropyl, n-, iso-, sec- or tert-butyl group,
  X represents a hydrogen atom, a fluorine, chlorine, bromine or iodine atom, a nitro, methyl, methoxy, ethyl, ethoxy, n-propyl, n-propoxy, isopropyl, isopropoxy or n-, iso-, sec- or tert-butyl or -butoxy group, and a and n are each independently 1 or 2.

If 4-(4-trifluoromethylphenoxy)phenol and 2-benzyloxyethyl 2-bromo propionate are used as starting materials, the course of reaction variant (a) according to the present invention is illustrated by the following equation:

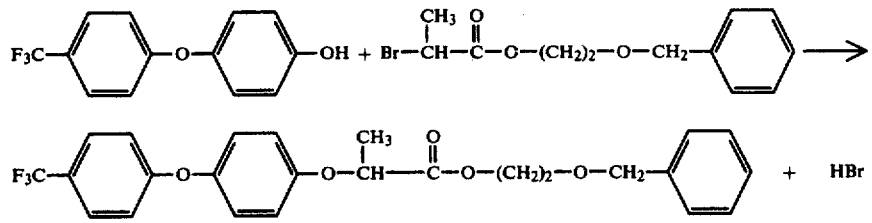

If 2-[4-(3,5-dichloro-2-pyridyloxy)phenoxy]propionyl chloride and 1-benzyloxy-2-propanol are used as starting materials, the course of reaction variant (b) according to the present invention is illustrated by the following equation:

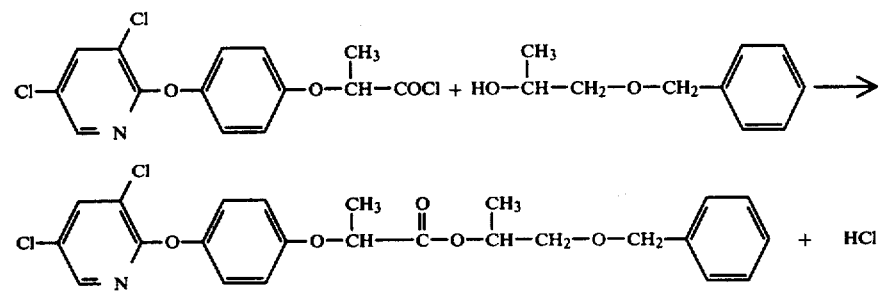

If 4-trifluoromethylphenylchloride and 2-(2-fluorobenzyloxy)ethyl-2-(4-hydroxyphenoxy)propionate are used as starting materials, the course of reaction variant (c) according to the present invention is illustrated by the following equation:

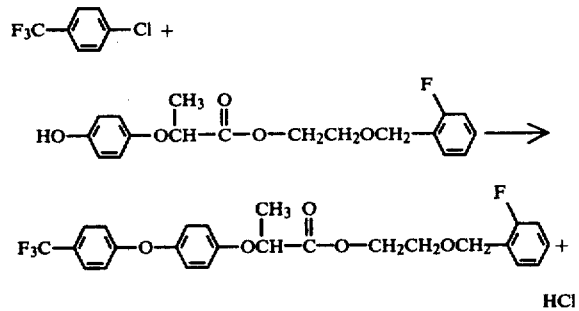

Examples of the compounds of the formula (II) used as starting materials in reaction variant (a) according to the present invention are 4-(4-trifluoromethylphenoxy)phenol, 4-(2-trifluoromethylphenoxy)phenol, 4-(4-fluorophenoxy)phenol, 4-(2,4-dichlorophenoxy)phenol, 4-(2-chloro-4-nitrophenoxy)phenol, 4-(2-trifluoromethyl-4-chlorophenoxy)phenol, 4-(4-trifluoromethyl-2-chlorophenoxy)phenol, 4-(3,5-dichloro-2-pyridyloxy)phenol, 4-(5-nitro-2-pyridyloxy)phenol, 4-(4-nitrophenoxy)phenol, 4-(4-bromo-2-chlorophenoxy)phenol, 4-(4-trifluoromethyl-2-nitrophenoxy)phenol, 4-(2,6-dichloro-4-trifluoromethylphenoxy)phenol, 4-(2-cyano-4-trifluoromethylphenoxy)phenol, 4-(2-chloro-4-cyanophenoxy)phenol, 4-(3-chloro-5-nitro-2-pyridyloxy)phenol, 4-(5-trifluoromethyl-2-pyridyloxy)phenol, 4-(3-chloro-5-trifluoromethyl-2-pyridyloxy)phenol, 4-(5-bromo-3-chloro-2-pyridyloxy)phenol, and 4-(4-chloro-2-methylphenoxy)phenol; as well as the alkali metal (e.g. Li, Na and K) salts thereof.

Examples of the other starting materials of the formula (III) for use in reaction variant (a) are:

2-benzyloxyethyl-2-chloro(or bromo)propionate, 3-benzyloxypropyl 2-chloro(or bromo)propionate, 1-methyl-2-benzyloxyethyl 2-chloro(or bromo)propionate, 2-α-methylbenzyloxyethyl 2-chloro(or bromo)propionate, 2-(2-fluorobenzyloxy)ethyl 2-chloro(or bromo)propionate, 2-(4-fluorobenzyloxy)ethyl 2-chloro(or bromo)propionate, 2-(2-chlorobenzyloxy)ethyl 2-chloro(or bromo)propionate, 2-(4-chlorobenzyloxy)ethyl 2-chloro(or bromo)propionate, 2-(2,4-dichlorobenzyloxy)ethyl 2-chloro(or bromo)propionate, 2-(3,4-dichlorobenzyloxy)ethyl 2-chloro(or bromo)propionate, 2-(2,6-dichlorobenzyloxy)ethyl 2-chloro(or bromo)propionate, 2-(2-methylbenzyloxy)ethyl 2-chloro(or bromo)propionate, 2-(3-nitrobenzyloxy)ethyl 2-chloro(or bromo)propionate, 2-(4-methoxybenzyloxy)ethyl 2-chloro(or bromo)propionate, 2-(4-bromobenzyloxy)ethyl 2-chloro(or bromo)propionate, 1-methyl-2-α-methylbenzyloxyethyl 2-chloro(or bromo)propionate, 2-(3-chlorobenzyloxy)ethyl 2-chloro(or bromo)propionate, 2-(2-bromobenzyloxy)ethyl 2-chloro(or bromo)propionate, 2-(3-fluorobenzyloxy)ethyl 2-chloro(or bromo)propionate, 1-methyl-2-(2-fluorobenzyloxy)ethyl 2-chloro(or bromo)-propionate, 3-(2-fluorobenzyloxy)propyl 2-chloro(or bromo)propionate, 2-(2-nitrobenzyloxy)ethyl 2-chloro(or bromo)propionate, 2-(4-nitrobenzyloxy)ethyl 2-chloro(or bromo)propionate, 2-(4-methylbenzyloxy)ethyl 2-chloro(or bromo)propionate, 2-(2-methoxybenzyloxy)ethyl 2-chloro(or bromo)propionate, and 3-(4-fluorobenzyloxy)propyl 2-chloro(or bromo)propionate.

Reaction variant (a) according to the present invention is preferably carried out in a presence of a diluent. For this purpose, any inert solvents may be employed.

Example of such solvents and diluents include water; aliphatic, alicyclic and aromatic hydrocarbons—each of which may optionally be chlorinated (such as hexane, cyclohexane, petroleum ether, ligroin, benzene, toluene, xylene, methylene chloride, chloroform, carbon tetrachloride, ethylene chloride, tri-chloroethylene, and chlorobenzene), ethers (such as diethyl ether, methyl ethyl ether, diisopropyl ether, dibutyl ether, propylene oxide, dioxane, and tetrahydrofuran), kenotes (such as acetone, methyl ethyl ketone, methyl i-propyl ketone, and methyl isobutyl ketone), nitriles (such as acetonitrile, propionitrile, and acrylonitrile), alcohols (such as methanol, ethanol, iso-propanol, butanol, and ethylene glycol), esters (such as ethyl acetate and amyl acetate), acid amides (such as dimethylformamide and dimethylacetamide) sulfones and sulfoxides (such as dimethylsulfoxide and sulfolane) and bases (such as pyridine).

The reaction variant (a) is preferably carried out in the presence of an acid-binding agent. As example of such acid-binding agents, there may be mentioned hydroxides, carbonates, bicarbonates and alcoholates of alkali metals, and tertiary amines such as triethylamine, diethylaniline, pyridine.

Reaction variant (a) can be carried out over a wide range of temperatures. Generally, it is carried out at a temperature between −20° C. and the boiling point of the reaction mixture, preferably between 0° C. and 100° C.

This reaction variant(a) is preferably carried out under ambient pressure, although it can be effected under elevated or reduced pressure.

Examples of the compounds of the formula (IV) used as starting materials in reaction variant (b) are: 2-[4-(4-trifluoromethylphenoxy)phenoxy]propionyl chloride, 2-[4-(2-trifluoromethylphenoxy)phenoxy]propionyl chloride, 2-[4-(4-fluorophenoxy)phenoxy]propionyl chloride, 2-[4-(2,4-dichlorophenoxy)phenoxy]propionyl chloride, 2-[4-(2-chloro-4-nitrophenoxy)phenoxy]propionyl chloride, 2-[4-(2-trifluoromethyl-4-chlorophenoxy)phenoxy]propionyl chloride, 2-[4-(3,5-dichloro-2-pyridyloxy)phenoxy]propionyl chloride, 2-[4-(4-trifluoromethyl-2-chlorophenoxy)phenoxy]propionyl chloride, 2-[4-(5-nitro-2-pyridyloxy)phenoxy]propionyl chloride, 2-[4-(4-nitrophenoxy)phenoxy]propionyl chloride, 2-[4-(4-bromo-2-chlorophenoxy)phenoxy]propionyl chloride, 2-[4-(4-trifluoromethyl-2-nitrophenoxy)phenoxy]propionyl chloride, 2-[4-(2,6-dichloro-4-trifluoromethylphenoxy)phenoxy]propionyl chloride, 2-[4-(2-cyano-4-trifluoromethylphenoxy)phenoxy]propionyl chloride, 2-[4-(2-chloro-4-cyanophenoxy)phenoxy]propionyl chloride, 2-[4-(3-chloro-5-nitro-2-pyridyloxy)phenoxy]propionyl chloride, 2-[4-(5-trifluoromethyl-2-pyridyloxy)phenoxy]-propionyl chloride, 2-[4-(3-chloro-5-trifluoromethyl-2-pyridyloxy)phenoxy]propionyl chloride, 2-[4-(5-bromo-3-chloro-2-pyridyloxy)phenoxy]propionyl chloride, and 2-[4-(4-chloro-2-methylphenoxy)phenoxy]propionyl chloride; as well as the corresponding bromides or free propionic acid derivatives.

Examples of the other starting materials of the formula (V) for use in reaction variant (b) are: 2-benzyloxyethanol, 3-benzyloxypropanol, 1-benzyloxy-2-propanol, 2-α-methylbenzyloxyethanol, 2-(2-fluorobenzyloxy)ethanol, 2-(4-fluorobenzyloxy)ethanol, 2-(2-chlorobenzyloxy)ethanol, 2-(4-chlorobenzyloxy)ethanol, 2-(2,4-dichlorobenzyloxy)ethanol, 2-(3,4-dichlorobenzyloxy)ethanol, 2-(2,6-dichlorobenzyloxy)ethanol, 2-(2-methylbenzyloxy)ethanol, 2-(3-nitrobenzyloxy)ethanol, 2-(4-methoxybenzyloxy)ethanol, 2-(4-bromobenzyloxy)ethanol, 1-(α-methylbenzyloxy)-2-propanol, 2-(3-chlorobenzyloxy)ethanol, 2-(2-bromobenzyloxy)ethanol, 2-(3-fluorobenzyloxy)ethanol, 1-(2-fluorobenzyloxy)-2-propanol, 3-(2-fluorobenzyloxy)propanol, 2-(2-nitrobenzyloxy)ethanol, 2-(4-nitrobenzyloxy)ethanol, 2-(4-methylbenzyloxy)ethanol, 2-(2-methoxybenzyloxy)ethanol, and 3-(4-fluorobenzyloxy)propanol.

In carrying out reaction variant (b) any of the inert solvents or diluents as described hereinbefore for reaction variant (a) is preferably used to obtain the end product with high purity in high yield. Likewise reaction variant (b) is preferably carried out in the presence of an acid-binding agent as described hereinbefore for reaction variant (a).

Reaction variant (b) can be carried within the same reaction conditions of temperature and pressure as those mentioned hereinbefore for reaction variant (a).

Examples of the compounds of the formula (VI) used as starting materials in reaction variant (c) are: 4-(or 2-)trifluoromethyl chloro (or bromo)benzene, 1-chloro-4-fluorobenzene, 1,2,4-trichlorobenzene, 1-bromo-2,4-dichlorobenzene, 3,4-dichloro-nitrobenzene, 4-bromo-3-chloro-nitrobenzene, 1,4-dichloro-2-trifluoromethylbenzene, 1-bromo-4-chloro-2-trifluoromethylbenzene, 1,2-dichloro-4-trifluoromethylbenzene, 1-bromo-2-chloro-4-trifluoromethylbenzene, 2,3,5-trichloropyridine, 2-bromo-3,5-dichloropyridine, 2-chloro(or bromo)-5-nitropyridine, 4-chloro(or bromo)nitrobenzene, 1-bromo-3,4-dichlorobenzene, 2-chloro-1,4-dibromobenzene, 2-chloro(or bromo)-5-trifluoromethylnitrobenzene, 1,2,3-trichloro-5-trifluoromethylbenzene, 1-bromo-2,6-dichloro-4-trifluoromethylbenzene, 2-chloro(or bromo)-5-trifluoromethyl benzonitrile, 3,4-dichlorobenzonitrile, 4-bromo-3-chloro benzonitrile, 2,3-dichloro-5-nitropyridine, 2-bromo-3-chloro-5-nitropyridine, 2-chloro(or bromo)-5-trifluoromethylpyridine, 2,3-dichloro-5-trifluoromethylpyridine, 2-bromo-3-chloro-5-trifluoromethylpyridine, 5-bromo-2,3-dichloropyridine, 3-chloro-2,5-dibromopyridine, 2,5-dichlorotoluene and 2-bromo-5-chlorotoluene.

Example of the other starting materials of the formula (VII) also used in reaction variant (c) are: 2-benzyloxyethyl 2-(4-hydroxyphenoxy)propionate, 3-benzyloxypropyl 2-(4-hydroxyphenoxy)propionate, 1-methyl-2-benzyloxyethyl 2-(4-hydroxyphenoxy)propionate, 2-α-methylbenzyloxyethyl 2-(4-hydroxyphenoxy)propionate, 2-(2-fluorobenzyloxy)ethyl 2-(4-hydroxyphenoxy)propionate, 2-(4-fluorobenzyloxy)ethyl 2-(4-hydroxyphenoxy)propionate, 2-(2-chlorobenzyloxy)ethyl 2-(4-hydroxyphenoxy)propionate, 2-(4-chlorobenzyloxy)ethyl 2-(4-hydroxyphenoxy)propionate, 2-(2,4-dichlorobenzyloxy)ethyl 2-(4-hydroxyphenoxy)propionate, 2-(3,4-dichlorobenzyloxy)ethyl 2-(4-hydroxyphenoxy)propionate, 2-(2,6-dichlorobenzyloxy)ethyl 2-(4-hydroxyphenoxy)propionate, 2-(2-methylbenzyloxy)ethyl 2-(4-hydroxyphenoxy)propionate, 2-(3-nitrobenzyloxy)ethyl 2-(4-hydroxyphenoxy)propionate, 2-(4-methoxybenzyloxy)ethyl 2-(4-hydroxyphenoxy)propionate, 2-(4-bromobenzyloxy)ethyl 2-(4-hydroxyphenoxy)propionate, 1-methyl-2-α-methylbenzyloxyethyl 2-(4-hydroxyphenoxy)propionate, 2-(3-chlorobenzyloxy)ethyl 2-(4-hydroxyphenoxy)propionate, 2-(2-bromobenzyloxy)ethyl 2-(4-hydroxyphenoxy)propionate, 2-(3-fluorobenzyloxy)ethyl2-(4-hydroxyphenoxy)propionate, 1-methyl-2-(2-fluorobenzyloxy)ethyl 2-(4-hydroxyphenoxy)propionate, 3-(2-fluorobenzyloxy)propyl 2-(4-hydroxyphenoxy)propionate, 2-(2-nitrobenzyloxy)ethyl 2-(4-hydroxyphenoxy)propionate, 2-(4-nitrobenzyloxy)ethyl 2-(4-hydroxyphenoxy)propionate, 2-(2-methoxybenzyloxy)ethyl 2-(4-hydroxyphenoxy)propionate, 3-(4-fluorobenzyloxy)propyl 2-(4-hydroxyphenoxy)-propionate, and 2-(4-methylbenzyloxy)ethyl 2-(4-hydroxyphenoxy)propionate; as well as the alkali metal (e.g. Li, Na and K) salts thereof.

In carrying out reaction variant (c) any of the inert solvents or diluents as described hereinbefore for reaction variant (a) is preferably used to obtain the end product with high purity in high yield. Likewise reaction variant (c) is preferably carried out in the presence of an acid-binding agent as described hereinbefore for reaction variant (a).

Reaction variant (c) can be carried within the same reaction conditions of temperature and pressure as those mentioned hereinbefore for reaction variant (a).

The intermediate compound of the formula (III), (which may also be used as an intermediate in the production of intermediates of the formula (VII)) have not hitherto been disclosed in the literature and form a further subject of the present invention.

Thus, the present invention further provides a process for the production of a compound of the general formula (III), which comprises reacting a compound of the general formula $$Z^1-\underset{\underset{CH_3}{|}}{CH}-\underset{\underset{O}{||}}{C}-Z^2 \qquad (VIII)$$

in which $Z^1$ and $Z^2$ have the meanings given above, with a compound of the general formula

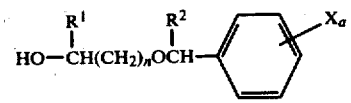

(IX)

in which $R^1$, $R^2$, X, a and n have the meanings given above.

Examples of the compounds of the formula (VIII) used as starting materials in the production of compounds of formula (III) are: 2-bromopropionic acid and 2-chloropropionic acid; as well as acyl chloride and acyl bromide thereof.

Examples of the other starting materials of the formula (IX) also used in the production of compounds of formula (III) are:

2-benzyloxyethanol, 3-benzyloxypropanol, 1-methyl-2-benzyloxyethanol, 2-α-methyl benzyloxyethanol, 2-(2-chlorobenzyloxy)ethanol, 2-(3-chlorobenzyloxy)ethanol, 2-(4-chlorobenzyloxy)ethanol, 2-(2,4-dichlorobenzyloxy)ethanol, 2-(2,6-dichlorobenzyloxy)ethanol, 2-(3,4-dichlorobenzyloxy)ethanol, 2-(2-methylbenzyloxy)ethanol, 2-(4-methylbenzyloxy)ethanol, 2-(2-methoxybenzyloxy)ethanol, 2-(4-methoxybenzyloxy)ethanol, 2-(2-bromobenzyloxy)ethanol, 2-(4-bromobenzyloxy)ethanol, 1-methyl-2-α-methylbenzylethanol, 2-(2-fluorobenzyloxy)ethanol, 2-(3-fluorobenzyloxy)ethanol, 2-(4-fluorobenzyloxy)ethanol, 2-(2-nitrobenzyloxy)ethanol, 2-(3-nitrobenzyloxy)ethanol, 2-(4-nitrobenzyloxy)ethanol, 1-methyl-2-(2-fluorobenzyloxy)ethanol, 3-(2-fluorobenzyloxy)propanol, 3-(4-fluorobenzyloxy)propanol.

If 2-bromopropionyl bromide and 2-benzyloxyethanol are used as starting materials, the course of the reaction for the production of compounds of formula (III) is illustrated by the following equation:

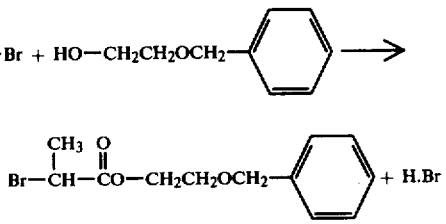

In the process for the production of compounds of formula (III) any of the inert solvents or diluents as described hereinbefore for reaction variant (a) is preferably used to obtain the end products with high purity in high yield. Likewise this reaction is preferably carried out in the presence of the acid-binding agent as described hereinbefore for reaction variant (a).

The reaction conditions of temperature and pressure are also chosen from those mentioned hereinbefore for reaction variant (a).

The starting compounds of formula (VII) are also novel and form a further subject of the present invention.

The present invention further provides a process for the production of a compound of the formula (VII), which comprises reacting a compound of the formula

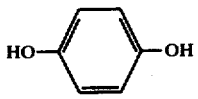

with a compound of the general formula

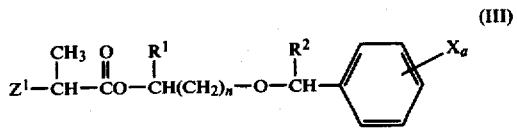

(III)

in which $R^1$, $R^2$, X, a, n and $Z^1$ have the meanings given above.

Example of the compounds of the formula (III) used as starting materials have already been mentioned as preferred starting materials for reaction variant (a) and can be prepared as described above.

If hydroquinone and 2-benzyloxyethyl-2-bromopropionate are used as starting materials, the course of the reaction for the production of compounds of formula (VII) is illustrated by the following equation:

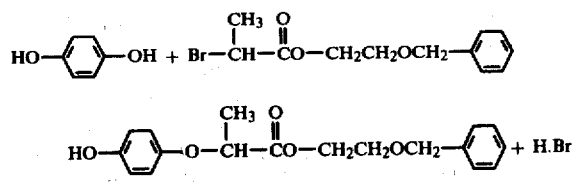

In the process for the production of compounds of formula (VII) any of the inert solvents or diluents as described hereinbefore for reaction variant (a) is preferably used to obtain the end products with high purity in high yield. Likewise this reaction is preferably carried out in the presence of the acid-binding agent as described hereinbefore for reaction variant (a).

The reaction conditions of temperature and pressure are also chosen from those mentioned hereinbefore for reaction variant (a).

The active compounds of formula (I) according to the present invention show excellent selective herbicidal effect when used as soil-treating agents to be used pre- or post-emergence of gramineous weeds.

Since the active compounds according to the present invention show little or no toxicity towards warm-blooded animals and show good selectivity for agricultural plants, that is, cause no phytotoxicity for agricultural plants, they can be conveniently used as herbicides for controlling weeds.

The active compounds according to the invention influence plant growth and can therefore be used as defoliants, desiccants, agents for destroying broad-leaved plants, germination inhibitors and, especially, as weed-killers. By "weeds" in the broadest sense there are meant plants growing in places where they are not desired.

Whether the compounds according to the invention act as total herbicides or selective herbicides depends essentially on the amount used.

The active compounds according to the present invention may be used, for example, to combat the following plants: dicotyledon weeds of the genera Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduxs, Sonchus, Rorippa, Rotala, Lindernia, Lamium, Veronica, Abutilon, Emex, Datura, Viola, Galeopsis, Papaver, Centaurea and Solanum; and monocotyledon weeds of the genera Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

The active compounds according to the present invention may be used, for example, as selective herbicides in the following cultures:

dicotyledon cultures of the genera Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita; and monocotyledon cultures of the genera Oryza, Zea, Triticum, Hordeum, Avena, Secale, Sorghum, Panicum, Saccharum, Ananas, Asparagus and Allium.

However, the use of the active compounds according to the invention is in no way restricted to these genera but also embraces other plants, in the same way.

Depending on the concentrations, the compounds can be used for the total combating of weeds, for example on industrial terrain and railway tracks and on paths and squares with or without trees. Equally, the compounds can be employed for combating weeds in perennial cultures, for example afforestations, decorative tree plantings, orchards, vineyards, citrus groves, nut orchards, banana plantations, coffee plantations, tea plantations, rubber plantations, oil palm plantations, cacao plantations, soft fruit plantings and hopfields, and for the selective combating of weeds in annual cultures.

The active compounds according to the present invention may particularly be used to combat the following plants: *Echinochloa crusgalli, Digitaria adscendeno, Eleusine indica, Setaria viridis, Avena fatua, Alopecurus aequalis, Setaria lutescens, Agropyron repens* or *Agropyron tsukushiense*.

In addition, they show excellent herbicidal and re-growth-control effects on, for example, Sorghum halepense or Cynodon dactylon.

The active compounds can be converted into the customary formulations, such as solutions, emulsions, wettable powders, suspensions, dusting agents, soluble powders, granules, suspension-emulsion concentrates, natural and synthetic materials impregnated with active compound, and very fine capsules in polymeric substances.

These formulations may be produced in known manner, for example by mixing the active compounds with extenders, that is to say liquid or solid diluents or carriers, optionally with the use of surface-active agents, that is to say emulsifying agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.001 to 100 percent by weight of active compound, preferably from 0.005 to 95 percent by weight.

The active compounds according to the invention, as such or in the form of their formulations, can also be used, for combating weeds, as mixtures with known herbicides, finished formulations or tank mixing being possible. Mixtures with other known active compounds, such as fungicides, insecticides, acaricides, nematicides, bird repellants, growth factors, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They may be used in the customary manner, for example by watering, spraying, atomising, scattering or dusting.

The amount of active compound in the ready-to-use preparations can vary widely according to circumstance. However, it is in general from 0.01 to 95 percent, preferably from 0.05 to 60 percent by weight.

The compounds can also be used in the ultra-low-volume method, wherein the preparation used can contain up to 100% of the active ingredient.

The active compounds can be applied after emergence of the plants or before emergence of the plants, that is to say by the pre-emergence method. They can also be incorporated into the soil before sowing.

The amount of active compound used can vary within a substantial range. It depends essentially on the nature of the desired effect. In general, the amounts used are between 0.01 and 2 kg of active compound per hectare, preferably between 0.05 and 1 kg/ha.

The present invention also provides a herbicidal composition containing as active ingredient a compound of the present invention in admixture with a solid diluent or carrier or in admixture with a liquid diluent or carrier containing a surface-active agent.

The present invention also provides a method of combating weeds which comprises applying to the weeds, or to a habitat thereof, a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

Compositions according to this invention are illustrated in the following Examples.

In these Examples, the compounds according to the present invention are each identified by the number (given in brackets) of the corresponding preparative Example. References to "parts" are to be understood as meaning parts by weight.

EXAMPLE i

Fifteen parts of compound (I), 80 parts of a 1:5 mixture of powdered diatomaceous earth and powdered clay, 2 parts of sodium alkylbenzenesulfonate and 3 parts of sodium alkylnaphthalenesulfonate/formaldehyde condensate were ground and mixed to form a wettable powder. The wettable powder was diluted with water before use.

EXAMPLE ii

Thirty parts of compound (11), 55 parts of xylene, 8 parts of polyoxyethylene alkylphenyl ether and 7 parts of calcium alkylbenzenesulfonate were mixed with stirring to form an emulsifiable concentrate. The emulsifiable concentrate was diluted with water before use.

EXAMPLE iii

Two parts of compound (12) and 98 parts of powdered clay were pulverized and mixed to form a dusting agent.

EXAMPLE iv 1.5 parts of compound (13), 0.5 part of isopropyl hydrogen phosphate (PAP) and 98 parts of powdered clay were ground and mixed to form a dusting agent.

EXAMPLE v 25 parts of water were added to, and thoroughly mixed with, a mixture of 10 parts of compound (14), 30 parts of bentonite (montmorillonite), 58 parts of talc and 2 parts of lignin sulfonate. The resultant mixture was formed into granules having a size of 10 to 40 mesh by means of an extrusion-type granulator, and dried at 40° to 50° C. to form granules.

EXAMPLE vi

A rotary mixer was charged with 95 parts of clay mineral particles having a particle size distribution in the range of 0.2 to 2 mm, and, while rotating the mixer, 5 parts of compound (2) dissolved in an organic solvent were sprayed uniformly onto the clay mineral particles. The particles were then dried at 40° to 50° C. to form granules.

The herbicidal activity of the compounds of the formula (I) is illustrated by the following biotest Examples.

In these Examples, the compounds according to the present invention are each identified by the number (given in brackets) of the corresponding preparative Example.

The known comparison compound is identified as follows:

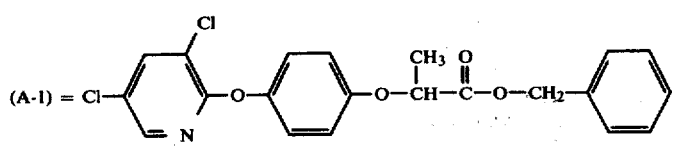

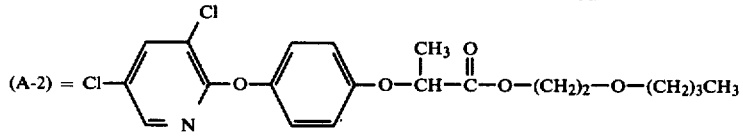

(They are described in Japanese Laid-open Patent Application No. 51-106,735).

(B-1) =

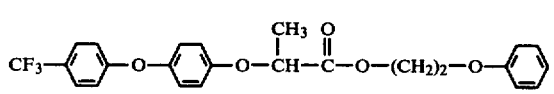

(A compound described in Japanese Laid-open Patent Application No. 52-131,545).

(C-1) =

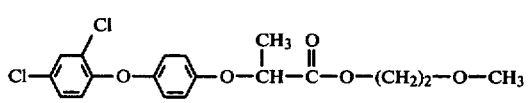

(A compound described in Japanese Laid-open Patent Application No. 52-144,637).

(D-1) =

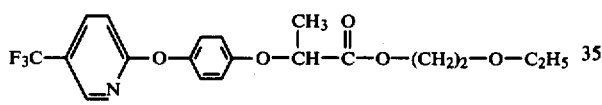

(A compound described in Japanese Laid-open Patent Application No. 54-119,476).

EXAMPLE A

Pre-emergence Treatment Tests for Weeds and Crops in Upland Fields

Preparation of active compound:
Carrier: 5 parts by weight of acetone
Emulsifier: 1 part by weight of benzyloxy polyglycol ether A preparation of the active compound was obtained as an emulsifiable concentrate by mixing 1 part by weight of the active compound with the aforesaid amounts of the carrier and the emulsifier. A predetermined amount of the preparation was obtained by dilution with water.

Testing method:

Field soils placed in 1,000 cm² pots were respectively seeded with Arachis, Pisum, Gossypium and Glycine in a greenhouse, and covered with a soil mixed with seeds of *Agropyron repens*, *Echinochloa crus-galli* and *Setaria lutescens* in a depth of 1 cm. One day after the seeding, 10 ml of the above-prepared solutions respectively containing 500 ppm, 200 ppm, 100 ppm, and 50 ppm active ingredient were uniformly applied to the soil surface layer.

4 weeds after the treatment, the herbicidal effect and degree of phytotoxicity were evaluated on a scale of from 0 to 10 in accordance with the following standards.

The herbicidal effect was evaluated as follows in comparison with an untreated control.

| Rating | Weed-kill ratio based on the control |
|---|---|
| 10 | 100% (withered) |
| 9 | at least 90% but less than 100% |
| 8 | at least 80% but less than 90% |
| 7 | at least 70% but less than 80% |
| 6 | at least 60% but less than 70% |
| 5 | at least 50% but less than 60% |
| 4 | at least 40% but less than 50% |
| 3 | at least 30% but less than 40% |
| 2 | at least 20% but less than 30% |
| 1 | at least 10% but less than 20% |
| 0 | less than 10% (not effective) |

The phytotoxicity towards the crops was evaluated as follows in comparison with the untreated control.

| Rating | Phytotoxicity rate in comparison with the control |
|---|---|
| 10 | at least 90% (fatal damage) |
| 9 | at least 80% but less than 90% |
| 8 | at least 70% but less than 80% |
| 7 | at least 60% but less than 70% |
| 6 | at least 50% but less than 60% |
| 5 | at least 40% but less than 50% |
| 4 | at least 30% but less than 40% |
| 3 | at least 20% but less than 30% |
| 2 | at least 10% but less than 20% |
| 1 | more than 0% but less than 10% |
| 0 | 0% (no phytotoxicity) |

The test results are shown in Table 1 in which the symbols a to g represent the following weeds and crops:
a: *Agropyron repens*
b: *Echinochloa crus-galli*
c: *Setaria lutescens*
d: Arachis
e: Pisum
f: Gossypium
g: Glycine

TABLE 1

| Compound No. | Amount of Effective Ingredient kg/ha | Herbicidal Effect Weed | | | Phytotoxicity Crop | | | |
|---|---|---|---|---|---|---|---|---|
| | | a | b | c | d | e | f | g |
| 1 | 0.5 | 10 | 10 | 10 | 0 | 0 | 0 | 0 |
| | 0.2 | 10 | 10 | 10 | 0 | 0 | 0 | 0 |
| | 0.1 | 8 | 9 | 10 | 0 | 0 | 0 | 0 |
| | 0.05 | 6 | 7 | 9 | 0 | 0 | 0 | 0 |
| 3 | 0.5 | 10 | 10 | 10 | 0 | 0 | 0 | 0 |
| | 0.2 | 10 | 10 | 10 | 0 | 0 | 0 | 0 |
| | 0.1 | 8 | 9 | 10 | 0 | 0 | 0 | 0 |
| | 0.05 | 6 | 7 | 9 | 0 | 0 | 0 | 0 |
| 4 | 0.5 | 10 | 10 | 10 | 0 | 0 | 0 | 0 |
| | 0.2 | 10 | 10 | 10 | 0 | 0 | 0 | 0 |
| | 0.1 | 8 | 9 | 9 | 0 | 0 | 0 | 0 |
| | 0.05 | 6 | 7 | 8 | 0 | 0 | 0 | 0 |
| 36 | 0.5 | 10 | 10 | 10 | 0 | 0 | 0 | 0 |
| | 0.2 | 10 | 9 | 10 | 0 | 0 | 0 | 0 |
| | 0.1 | 8 | 8 | 9 | 0 | 0 | 0 | 0 |
| | 0.05 | 6 | 7 | 8 | 0 | 0 | 0 | 0 |
| 37 | 0.5 | 10 | 10 | 10 | 0 | 0 | 0 | 0 |

TABLE 1-continued

| | Amount of Effective Ingredient kg/ha | Herbicidal Effect Weed | | | Phytotoxicity Crop | | | |
|---|---|---|---|---|---|---|---|---|
| | | a | b | c | d | e | f | g |
| | 0.2 | 10 | 10 | 10 | 0 | 0 | 0 | 0 |
| | 0.1 | 8 | 9 | 10 | 0 | 0 | 0 | 0 |
| | 0.05 | 7 | 8 | 9 | 0 | 0 | 0 | 0 |
| 38 | 0.5 | 10 | 10 | 10 | 0 | 0 | 0 | 0 |
| | 0.2 | 10 | 10 | 10 | 0 | 0 | 0 | 0 |
| | 0.1 | 8 | 9 | 10 | 0 | 0 | 0 | 0 |
| | 0.05 | 7 | 8 | 10 | 0 | 0 | 0 | 0 |
| 39 | 0.5 | 10 | 10 | 10 | 0 | 0 | 0 | 0 |
| | 0.2 | 10 | 10 | 10 | 0 | 0 | 0 | 0 |
| | 0.1 | 9 | 9 | 10 | 0 | 0 | 0 | 0 |
| | 0.05 | 8 | 8 | 9 | 0 | 0 | 0 | 0 |
| 29 | 0.5 | 10 | 10 | 10 | 0 | 0 | 0 | 0 |
| | 0.2 | 10 | 10 | 10 | 0 | 0 | 0 | 0 |
| | 0.1 | 10 | 10 | 10 | 0 | 0 | 0 | 0 |
| | 0.05 | 9 | 10 | 10 | 0 | 0 | 0 | 0 |
| 43 | 0.5 | 10 | 10 | 10 | 0 | 0 | 0 | 0 |
| | 0.2 | 10 | 10 | 10 | 0 | 0 | 0 | 0 |
| | 0.1 | 9 | 9 | 10 | 0 | 0 | 0 | 0 |
| | 0.05 | 8 | 7 | 9 | 0 | 0 | 0 | 0 |
| 14 | 0.5 | 10 | 10 | 10 | 0 | 0 | 0 | 0 |
| | 0.2 | 10 | 10 | 10 | 0 | 0 | 0 | 0 |
| | 0.1 | 8 | 8 | 9 | 0 | 0 | 0 | 0 |
| | 0.05 | 6 | 6 | 8 | 0 | 0 | 0 | 0 |
| 57 | 0.5 | 10 | 10 | 10 | 0 | 0 | 0 | 0 |
| | 0.2 | 10 | 10 | 10 | 0 | 0 | 0 | 0 |
| | 0.1 | 8 | 8 | 9 | 0 | 0 | 0 | 0 |
| | 0.05 | 6 | 6 | 8 | 0 | 0 | 0 | 0 |
| 62 | 0.5 | 10 | 10 | 10 | 0 | 0 | 0 | 0 |
| | 0.2 | 10 | 10 | 10 | 0 | 0 | 0 | 0 |
| | 0.1 | 10 | 10 | 10 | 0 | 0 | 0 | 0 |
| | 0.05 | 9 | 9 | 9 | 0 | 0 | 0 | 0 |
| 63 | 0.5 | 10 | 10 | 10 | 0 | 0 | 0 | 0 |
| | 0.2 | 10 | 10 | 10 | 0 | 0 | 0 | 0 |
| | 0.1 | 9 | 9 | 9 | 0 | 0 | 0 | 0 |
| | 0.05 | 8 | 8 | 9 | 0 | 0 | 0 | 0 |
| 64 | 0.5 | 10 | 10 | 10 | 0 | 0 | 0 | 0 |
| | 0.2 | 10 | 10 | 10 | 0 | 0 | 0 | 0 |
| | 0.1 | 9 | 9 | 9 | 0 | 0 | 0 | 0 |
| | 0.05 | 8 | 9 | 9 | 0 | 0 | 0 | 0 |
| 20 | 0.5 | 10 | 10 | 10 | 0 | 0 | 0 | 0 |
| | 0.2 | 10 | 10 | 10 | 0 | 0 | 0 | 0 |
| | 0.1 | 9 | 9 | 9 | 0 | 0 | 0 | 0 |
| | 0.05 | 8 | 8 | 9 | 0 | 0 | 0 | 0 |
| 22 | 0.5 | 10 | 10 | 10 | 0 | 0 | 0 | 0 |
| | 0.2 | 10 | 10 | 10 | 0 | 0 | 0 | 0 |
| | 0.1 | 9 | 9 | 9 | 0 | 0 | 0 | 0 |
| | 0.05 | 8 | 8 | 9 | 0 | 0 | 0 | 0 |
| 24 | 0.5 | 10 | 10 | 10 | 0 | 0 | 0 | 0 |
| | 0.2 | 10 | 10 | 10 | 0 | 0 | 0 | 0 |
| | 0.1 | 9 | 9 | 9 | 0 | 0 | 0 | 0 |
| | 0.05 | 8 | 8 | 8 | 0 | 0 | 0 | 0 |
| 71 | 0.5 | 10 | 10 | 10 | 0 | 0 | 0 | 0 |
| | 0.2 | 9 | 10 | 9 | 0 | 0 | 0 | 0 |
| | 0.1 | 8 | 9 | 9 | 0 | 0 | 0 | 0 |
| | 0.05 | 7 | 8 | 8 | 0 | 0 | 0 | 0 |
| 73 | 0.5 | 10 | 10 | 10 | 0 | 0 | 0 | 0 |
| | 0.2 | 10 | 10 | 10 | 0 | 0 | 0 | 0 |
| | 0.1 | 9 | 9 | 9 | 0 | 0 | 0 | 0 |
| | 0.05 | 8 | 9 | 9 | 0 | 0 | 0 | 0 |
| Comparative Compound | | | | | | | | |
| A-1 | 0.5 | 7 | 9 | 9 | 0 | 0 | 0 | 0 |
| | 0.2 | 5 | 7 | 8 | 0 | 0 | 0 | 0 |
| | 0.1 | 2 | 5 | 6 | 0 | 0 | 0 | 0 |
| | 0.05 | 0 | 2 | 4 | 0 | 0 | 0 | 0 |
| B-1 | 0.5 | 9 | 10 | 10 | 0 | 0 | 0 | 0 |
| | 0.2 | 7 | 8 | 8 | 0 | 0 | 0 | 0 |
| | 0.1 | 3 | 6 | 7 | 0 | 0 | 0 | 0 |
| | 0.05 | 0 | 3 | 4 | 0 | 0 | 0 | 0 |

EXAMPLE B

Foliage-Treating Tests for Weeds and Crops in Upland Fields

Field soils placed in 2,000 $cm^2$ pots were respectively seeded with Glycine, Rephanus and Beta, and covered with a soil mixed with seeds of *Echinochloa crus-galli*, *Digitaria adscendens*, *Eleusine indica*, *Setaria viridis*, *Avena fatua* and *Alopecurus aequalis* in a depth of 1 cm. 10 days after seeding (when weeds were on the average in a second leaf stage and when Glycine, Rephanus and Beta were in the initial stage of normal leaf-growing period), 20 ml of the solutions prepared as in Test Example 1 and respectively containing 500 ppm, 200 ppm, 100 ppm, and 50 ppm active ingredient were uniformly applied to the leaves of the plants to be tested.

3 weeds after the treatment, the herbicidal effect and degree of phytotoxicity were evaluated in the same manner as in Example A.

The test results are shown in Table 2 in which the symbols h to p represent the following weeds and crops:
h: *Echinochloa crus-galli*
i: *Digitaria adscendens*
j: *Eleusine indica*
k: *Setaria viridis*
l: *Avena fatua*
m: *Alopecurus aequalis*
n: Glycine
o: Rephanus
p: Beta

TABLE 2

| | Amount of Effective Ingredient kg/ha | Herbicidal Effect Weed | | | | | | Phytotoxicity Crop | | |
|---|---|---|---|---|---|---|---|---|---|---|
| | | h | i | j | k | l | m | n | o | p |
| Compound No. | | | | | | | | | | |
| 1 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 10 | 10 | 10 | 10 | 0 | 0 | 0 |
| | 0.05 | 10 | 10 | 10 | 10 | 10 | 10 | 0 | 0 | 0 |
| 2 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 10 | 10 | 10 | 10 | 0 | 0 | 0 |
| | 0.05 | 10 | 10 | 10 | 10 | 10 | 10 | 0 | 0 | 0 |
| 3 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 10 | 10 | 10 | 10 | 0 | 0 | 0 |
| | 0.05 | 10 | 10 | 10 | 10 | 9 | 10 | 0 | 0 | 0 |
| 4 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 9 | 9 | 9 | 9 | 10 | 0 | 0 | 0 |
| | 0.05 | 9 | 9 | 9 | 9 | 8 | 9 | 0 | 0 | 0 |
| 37 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 10 | 10 | 10 | 10 | 0 | 0 | 0 |
| | 0.05 | 10 | 10 | 10 | 10 | 10 | 10 | 0 | 0 | 0 |
| 38 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 10 | 10 | 10 | 10 | 0 | 0 | 0 |
| | 0.05 | 10 | 10 | 10 | 10 | 10 | 10 | 0 | 0 | 0 |
| 39 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 10 | 10 | 10 | 10 | 0 | 0 | 0 |
| | 0.05 | 10 | 10 | 10 | 10 | 10 | 10 | 0 | 0 | 0 |
| 29 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 10 | 10 | 10 | 10 | 0 | 0 | 0 |
| | 0.05 | 10 | 10 | 10 | 10 | 10 | 10 | 0 | 0 | 0 |
| 40 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 10 | 10 | 10 | 10 | 0 | 0 | 0 |
| | 0.05 | 10 | 10 | 10 | 10 | 10 | 10 | 0 | 0 | 0 |
| 41 | 0.5 | 10 | 10 | 10 | 10 | 10 | 10 | 0 | 0 | 0 |

TABLE 2-continued

| | Amount of Effective Ingredient kg/ha | Herbicidal Effect Weed | | | | | | Phytotoxicity Crop | | |
|---|---|---|---|---|---|---|---|---|---|---|
| | | h | i | j | k | l | m | n | o | p |
| | 0.2 | 10 | 10 | 10 | 10 | 10 | 10 | 0 | 0 | 0 |
| | 0.1 | 10 | 10 | 9 | 9 | 8 | 9 | 0 | 0 | 0 |
| | 0.05 | 9 | 9 | 8 | 8 | 7 | 8 | 0 | 0 | 0 |
| 43 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 10 | 10 | 10 | 10 | 0 | 0 | 0 |
| | 0.05 | 10 | 10 | 9 | 9 | 9 | 9 | 0 | 0 | 0 |
| 47 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 10 | 9 | 9 | 10 | 0 | 0 | 0 |
| | 0.05 | 9 | 10 | 9 | 8 | 7 | 9 | 0 | 0 | 0 |
| 48 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 9 | 9 | 8 | 9 | 0 | 0 | 0 |
| | 0.05 | 9 | 9 | 8 | 8 | 7 | 9 | 0 | 0 | 0 |
| 49 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 10 | 10 | 10 | 10 | 0 | 0 | 0 |
| | 0.05 | 10 | 10 | 10 | 10 | 10 | 10 | 0 | 0 | 0 |
| 50 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 10 | 10 | 9 | 10 | 0 | 0 | 0 |
| | 0.05 | 9 | 10 | 9 | 9 | 8 | 9 | 0 | 0 | 0 |
| 51 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 10 | 10 | 10 | 10 | 0 | 0 | 0 |
| | 0.05 | 10 | 10 | 10 | 10 | 9 | 10 | 0 | 0 | 0 |
| 54 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 10 | 10 | 10 | 10 | 0 | 0 | 0 |
| | 0.05 | 10 | 10 | 9 | 9 | 9 | 9 | 0 | 0 | 0 |
| 56 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 9 | 9 | 9 | 10 | 0 | 0 | 0 |
| | 0.05 | 9 | 9 | 8 | 8 | 8 | 9 | 0 | 0 | 0 |
| 57 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 9 | 9 | 9 | 9 | 10 | 0 | 0 | 0 |
| | 0.05 | 9 | 8 | 8 | 9 | 7 | 9 | 0 | 0 | 0 |
| 58 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 10 | 10 | 10 | 10 | 0 | 0 | 0 |
| | 0.05 | 10 | 9 | 10 | 9 | 9 | 9 | 0 | 0 | 0 |
| 16 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 10 | 10 | 10 | 10 | 0 | 0 | 0 |
| | 0.05 | 10 | 10 | 9 | 9 | 9 | 10 | 0 | 0 | 0 |
| 59 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 9 | 10 | 9 | 9 | 9 | 0 | 0 | 0 |
| | 0.05 | 9 | 7 | 9 | 9 | 8 | 9 | 0 | 0 | 0 |
| 60 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 9 | 9 | 9 | 9 | 9 | 10 | 0 | 0 | 0 |
| | 0.05 | 9 | 8 | 8 | 8 | 8 | 9 | 0 | 0 | 0 |
| 62 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 9 | 10 | 10 | 9 | 9 | 0 | 0 | 0 |
| | 0.05 | 9 | 8 | 9 | 9 | 9 | 9 | 0 | 0 | 0 |
| 17 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 9 | 10 | 10 | 10 | 10 | 0 | 0 | 0 |
| | 0.05 | 9 | 8 | 9 | 9 | 9 | 9 | 0 | 0 | 0 |
| 63 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 9 | 10 | 10 | 10 | 9 | 0 | 0 | 0 |
| | 0.05 | 10 | 8 | 9 | 9 | 9 | 9 | 0 | 0 | 0 |
| 64 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 8 | 10 | 10 | 9 | 9 | 0 | 0 | 0 |
| | 0.05 | 9 | 7 | 9 | 9 | 8 | 8 | 0 | 0 | 0 |
| 66 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 8 | 10 | 9 | 9 | 9 | 0 | 0 | 0 |
| | 0.05 | 9 | 7 | 9 | 9 | 8 | 8 | 0 | 0 | 0 |
| 67 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 10 | 10 | 9 | 10 | 0 | 0 | 0 |
| | 0.05 | 10 | 9 | 9 | 9 | 9 | 9 | 0 | 0 | 0 |
| 20 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 10 | 10 | 10 | 10 | 0 | 0 | 0 |
| | 0.05 | 10 | 9 | 9 | 9 | 9 | 9 | 0 | 0 | 0 |
| 21 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 10 | 10 | 10 | 10 | 0 | 0 | 0 |
| | 0.05 | 10 | 9 | 9 | 9 | 9 | 10 | 0 | 0 | 0 |
| 69 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 9 | 10 | 10 | 10 | 0 | 0 | 0 |
| | 0.05 | 9 | 9 | 9 | 9 | 9 | 9 | 0 | 0 | 0 |
| 70 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 9 | 9 | 10 | 9 | 9 | 0 | 0 | 0 |
| | 0.05 | 9 | 9 | 9 | 9 | 9 | 9 | 0 | 0 | 0 |
| 24 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 10 | 10 | 10 | 10 | 0 | 0 | 0 |
| | 0.05 | 10 | 9 | 9 | 9 | 9 | 10 | 0 | 0 | 0 |
| 25 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 10 | 10 | 10 | 10 | 0 | 0 | 0 |
| | 0.05 | 10 | 9 | 9 | 9 | 9 | 10 | 0 | 0 | 0 |
| 71 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 10 | 10 | 10 | 10 | 0 | 0 | 0 |
| | 0.05 | 10 | 9 | 10 | 10 | 9 | 9 | 0 | 0 | 0 |
| 27 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 10 | 10 | 10 | 10 | 0 | 0 | 0 |
| | 0.05 | 10 | 10 | 10 | 10 | 9 | 9 | 0 | 0 | 0 |
| 72 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 10 | 9 | 10 | 9 | 0 | 0 | 0 |
| | 0.05 | 10 | 9 | 9 | 9 | 9 | 9 | 0 | 0 | 0 |
| 23 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 10 | 10 | 10 | 10 | 0 | 0 | 0 |
| | 0.05 | 10 | 9 | 9 | 9 | 9 | 9 | 0 | 0 | 0 |
| 75 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 10 | 10 | 10 | 10 | 0 | 0 | 0 |
| | 0.05 | 10 | 9 | 9 | 9 | 9 | 9 | 0 | 0 | 0 |
| 77 | 0.5 | 10 | 10 | 10 | 10 | 10 | 10 | 0 | 0 | 0 |
| | 0.2 | 10 | 10 | 10 | 10 | 10 | 10 | 0 | 0 | 0 |
| | 0.1 | 10 | 10 | 10 | 10 | 10 | 10 | 0 | 0 | 0 |
| | 0.05 | 10 | 9 | 9 | 9 | 9 | 9 | 0 | 0 | 0 |
| Comparative Compound | | | | | | | | | | |
| A-2 | 0.5 | 10 | 10 | 10 | 10 | 9 | 10 | 0 | 0 | 0 |
| | 0.2 | 9 | 10 | 9 | 9 | 7 | 10 | 0 | 0 | 0 |
| | 0.1 | 7 | 8 | 6 | 7 | 5 | 8 | 0 | 0 | 0 |
| | 0.05 | 5 | 5 | 5 | 6 | 4 | 6 | 0 | 0 | 0 |
| C-1 | 0.5 | 10 | 10 | 9 | 10 | 9 | 10 | 0 | 0 | 0 |
| | 0.2 | 10 | 9 | 6 | 9 | 6 | 9 | 0 | 0 | 0 |
| | 0.1 | 7 | 5 | 3 | 6 | 3 | 6 | 0 | 0 | 0 |
| | 0.05 | 3 | 2 | 1 | 3 | 1 | 3 | 0 | 0 | 0 |

EXAMPLE C

Herbicidal and Regrowth-Control Tests for *Agropyron Tsukushiense*

Rice fields where *Agropyron tsukushiense* was gregarious was divided into 1 m² sections. 100 ml portions of solutions prepared as in Test Example 1 and respectively containing 1,000 ppm, 500 ppm, 200 ppm, and 100 ppm of the active ingredient were applied to the foliage of *Agropyron tsukusiense* in each section. 20 days after the treatment, the herbicidal effects were evaluated in the same manner as in Example A. Further, the effect of controlling regrowth of *Agropyron tsukusiense* was evaluated 40 days and 60 days after the treatment in accordance with the following standards.

| Rating | Regrowth-control ratio based on untreated section |
|---|---|
| 10 | 100% (complete control of regrowth) |
| 9 | at least 90% but less than 100% |
| 8 | at least 80% but less than 90% |
| 7 | at least 70% but less than 80% |
| 6 | at least 60% but less than 70% |
| 5 | at least 50% but less than 60% |
| 4 | at least 40% but less than 50% |
| 3 | at least 30% but less than 40% |
| 2 | at least 20% but less than 30% |
| 1 | at least 10% but less than 20% |
| 0 | less than 10% (no regrowth-control effect) |

The test results are shown in Table 3.

TABLE 3

| Compound No. | Amount of Effective Ingredient kg/ha | Herbicidal Effect 20 Days After Application | Regrowth-control Effect 40 Days After Application | Regrowth-control Effect 60 Days After Application |
|---|---|---|---|---|
| 1 | 1.0 | 10 | 10 | 10 |
| | 0.5 | 10 | 10 | 10 |
| | 0.2 | 10 | 10 | 10 |
| | 0.1 | 9 | 8 | 7 |
| 29 | 1.0 | 10 | 10 | 10 |
| | 0.5 | 10 | 10 | 10 |
| | 0.2 | 10 | 10 | 10 |
| | 0.1 | 9 | 8 | 7 |
| 57 | 1.0 | 10 | 10 | 10 |
| | 0.5 | 10 | 10 | 10 |
| | 0.2 | 10 | 10 | 9 |
| | 0.1 | 10 | 9 | 8 |
| 20 | 1.0 | 10 | 10 | 10 |
| | 0.5 | 10 | 10 | 10 |
| | 0.2 | 10 | 10 | 10 |
| | 0.1 | 9 | 9 | 8 |
| 21 | 1.0 | 10 | 10 | 10 |
| | 0.5 | 10 | 10 | 10 |
| | 0.2 | 10 | 10 | 10 |
| | 0.1 | 9 | 8 | 8 |
| 24 | 1.0 | 10 | 10 | 10 |
| | 0.5 | 10 | 10 | 10 |
| | 0.2 | 10 | 10 | 10 |
| | 0.1 | 9 | 8 | 7 |
| 73 | 1.0 | 10 | 10 | 10 |
| | 0.5 | 10 | 10 | 10 |
| | 0.2 | 10 | 10 | 9 |
| | 0.1 | 9 | 9 | 8 |
| 76 | 1.0 | 10 | 10 | 10 |
| | 0.5 | 10 | 10 | 10 |
| | 0.2 | 10 | 10 | 10 |
| | 0.1 | 9 | 8 | 7 |
| Comparative Compound | | | | |
| B-1 | 1.0 | 10 | 10 | 6 |
| | 0.5 | 7 | 6 | 3 |
| | 0.2 | 4 | 3 | 0 |
| | 0.1 | 1 | 0 | 0 |
| D-1 | 1.0 | 10 | 10 | 7 |
| | 0.5 | 9 | 7 | 2 |
| | 0.2 | 6 | 3 | 0 |
| | 0.1 | 3 | 0 | 0 |

EXAMPLE D

Herbicidal and Regrowth-Control Test for *Cynodon dactylon*

Upland field where *Cynodon dactylon* was gregarious was divided into 1 m² sections. The active ingredient in the same quantities as in Example C was treated to the *Cynodon dactylon*.

Herbicidal effect was evaluated 20 days after the treatment, and regrowth-control effect was evaluated 40 days and 60 days after the treatment in accordance with the same manner as in the foregoing Examples A to C.

The test results are shown in Table 4.

TABLE 4

| Compound No. | Amount of Effective Ingredient kg/ha | Herbicidal Effect 20 Days After Application | Regrowth-control Effect 40 Days After Application | Regrowth-control Effect 60 Days After Application |
|---|---|---|---|---|
| 1 | 1.0 | 10 | 10 | 10 |
| | 0.5 | 10 | 10 | 10 |
| | 0.2 | 10 | 10 | 10 |
| | 0.1 | 8 | 7 | 5 |
| 2 | 1.0 | 10 | 10 | 10 |
| | 0.5 | 10 | 10 | 10 |
| | 0.2 | 10 | 10 | 8 |
| | 0.1 | 10 | 8 | 7 |
| 4 | 1.0 | 10 | 10 | 10 |
| | 0.5 | 10 | 10 | 10 |
| | 0.2 | 10 | 10 | 9 |
| | 0.1 | 9 | 8 | 6 |
| 37 | 1.0 | 10 | 10 | 10 |
| | 0.5 | 10 | 10 | 10 |
| | 0.2 | 10 | 10 | 8 |
| | 0.1 | 9 | 8 | 7 |
| 20 | 1.0 | 10 | 10 | 10 |
| | 0.5 | 10 | 10 | 10 |
| | 0.2 | 10 | 9 | 8 |
| | 0.1 | 9 | 9 | 7 |
| 21 | 1.0 | 10 | 10 | 10 |
| | 0.5 | 10 | 10 | 10 |
| | 0.2 | 10 | 9 | 8 |
| | 0.1 | 9 | 8 | 7 |
| 74 | 1.0 | 10 | 10 | 10 |
| | 0.5 | 10 | 10 | 10 |
| | 0.2 | 10 | 9 | 8 |
| | 0.1 | 9 | 8 | 7 |
| 78 | 1.0 | 10 | 10 | 10 |
| | 0.5 | 10 | 10 | 10 |
| | 0.2 | 10 | 9 | 8 |
| | 0.1 | 9 | 7 | 6 |
| Comparative Compound | | | | |
| B-1 | 1.0 | 10 | 9 | 5 |
| | 0.5 | 8 | 5 | 2 |
| | 0.2 | 5 | 2 | 0 |
| | 0.1 | 4 | 0 | 0 |
| D-1 | 1.0 | 10 | 10 | 7 |
| | 0.5 | 9 | 7 | 5 |
| | 0.2 | 7 | 3 | 0 |
| | 0.1 | 5 | 1 | 0 |

Other compounds of the present invention employed in the foregoing Examples A to D were also confirmed to show excellent herbicidal effect in the same low amount as in the foregoing Examples A to D and to show regeneration-controlling effect on perennial gramineous weeds over a long period of time.

The following examples serve to illustrate processes for the production of compounds according to the present invention.

PREPARATIVE EXAMPLES

EXAMPLE 1

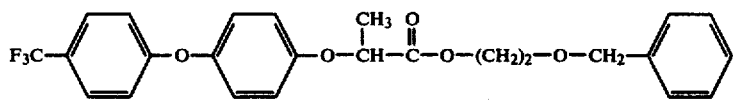
(1)

25.4 g of 4-(4-trifluoromethylphenoxy)phenol were added to 150 ml of dry acetonitrile, and 28.7 g of 2-benzyloxyethyl 2-bromopropionate and 14.5 g of anhydrous potassium carbonate were added thereto. Then, the mixture was refluxed for 4 hours, stirring well. After the completion of the reaction, acetonitrile was distilled off under reduced pressure.

Toluene was added to the residue, and the toluene layer was washed successively with 1% strength by weight sodium hydroxide aqueous solution and water. Upon distilling off toluene under reduced pressure, there were obtained 41 g of colourless, viscous end product, 2-benzyloxyethyl 2-(4-[4-trifluoromethylphenoxy)phenoxy]propionate. $n_D^{20}$ 1.5300.

EXAMPLE 2

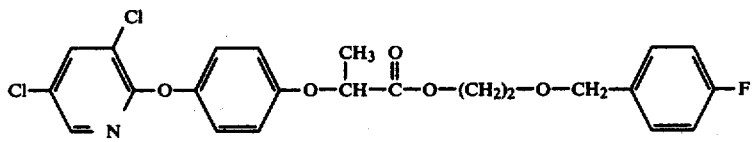
(2)

30.6 g of 4-(3,5-dichloro-2-pyridyloxy)phenol sodium salt and 30.5 g of 2-(4-fluorobenzyloxy)ethyl 2-chloropropionate were added to 100 ml of dimethylformamide, and the mixture was heated to 70° to 80° C. for 3 hours with stirring. After cooling to room temperature, the reaction solution was poured into 300 ml of water, then extracted with ether. The ether layer was washed successively with 1% strength by weight sodium hydroxide aqueous solution and water, followed by dehydration. Upon distilling off the ether, there were obtained 38 g of a pale yellow, viscous, oily end product, 2-(4-fluorobenzyloxy)ethyl 2-[4-(3,5-dichloro-2-pyridyloxy)phenoxy]propionate. $n_D^{20}$ 1.5643.

EXAMPLE 3

22.1 g of 2-(2,6-dichlorobenzyloxy)ethanol and 10.1 g of triethylamine were dissolved in 200 ml of toluene, then cooled to 0° C. To this solution was dropwise added a solution of 34.5 g of 2-[4-(4-trifluoromethylphenoxy)phenoxy]propionyl chloride in 50 ml of toluene at 0° to 10° C. After the dropwise addition, the reaction mixture was gradually heated and, at 40° C., it was stirred for one hour to complete the reaction. After cooling the reaction solution to room temperature, it was washed successively with 1% strength by weight sodium hydroxide aqueous solution and water, then dehydrated. After distilling off toluene under reduced pressure, the resulting colorless, viscous, oily product was allowed to stand for about 1 month to obtain 49.2 g of crystalline 2-(2,6-dichlorobenzyloxy)ethyl 2-[4-(4-trifluoromethylphenoxy)phenoxy]propionate. m.p. 51° to 53° C.

EXAMPLE 4

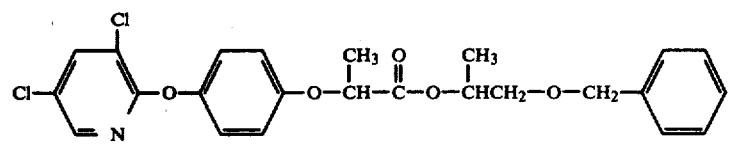
(4)

16.6 g of 1-benzyloxy-2-propanol and 10.6 g of triethylamine were dissolved in 200 ml of toluene, then cooled to 0° C. To this solution was dropwise added a solution of 34.7 g of 2-[4-(3,5-dichloro-2-pyridyloxy)phenoxy]propionyl chloride in 80 ml of toluene at 0° to 5° C. with stirring. After the dropwise addition, the mixture was gradually heated and, at 40° to 50° C., it was stirred for one hour to complete the reaction. After cooling to room temperature, it was washed successively with 1% strength by weight sodium hydroxide aqueous solution and water, followed by drying. Upon distilling off toluene under reduced pressure, there were obtained 43.3 g of pale yellow, viscous, oily 1-methyl-2-benzyloxyethyl 2-[4-(3,5-dichloro-2-pyridyloxy)phenoxy]propionate. $n_D^{20}$ 1.5710.

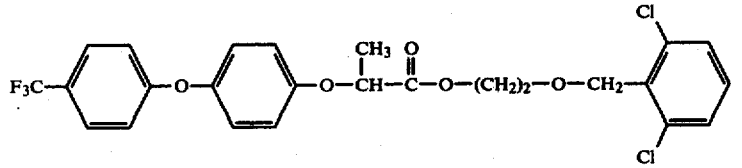
(3)

EXAMPLE 5

In the same manner as described in Example 1 or 2 but using starting materials given in the following table, there were synthesized the compounds of the present invention as shown in the table.

| Example No. | Starting Material | Starting Material | Product/Physical Constant |
|---|---|---|---|
| 6 | 4-(4-Trifluoromethyl-phenoxy)phenol | 1-Methyl-2-(2-fluorobenzyloxy)ethyl 2-chloropropionate | 1-Methyl-2-(2-fluorobenzyloxy)ethyl 2-[4-(4-trifluoromethylphenoxy)phenoxy]propionate |
| 7 | 4-(4-Trifluoromethyl-phenoxy)phenol | 3-(2-Fluorobenzyloxy)propyl 2-bromopropionate | 3-(2-Fluorobenzyloxy)propyl 2-[4-(4-trifluoromethylphenoxy)phenoxy]propionate |
| 8 | 4-(4-Trifluoromethyl-phenoxy)phenol sodium salt | 2-(3-Chlorobenzyloxy)-ethyl 2-chloropropionate | 2-(3-Chlorobenzyloxy)ethyl 2-[4-(4-trifluoromethylphenoxy)phenoxy]propionate |
| 9 | 4-(4-Trifluoromethyl-phenoxy)phenol sodium salt | 2-(2-Bromobenzyloxy)ethyl 2-chloropropionate | 2-(2-Bromobenzyloxy)ethyl 2-[4-(4-trifluoromethylphenoxy)phenoxy]propionate |
| 10 | 4-(4-Trifluoromethyl-phenoxy)phenol sodium salt | 2-(4-Methylbenzyloxy)-ethyl 2-bromopropionate | 2-(4-Methylbenzyloxy)ethyl 2-[4-(4-trifluoromethylphenoxy)phenoxy]propionate |
| 11 | 4-(4-Trifluoromethylphenoxy)-phenol sodium salt | 2-(2-Methoxybenzyloxy)-ethyl 2-bromopropionate | 2-(2-Methoxybenzyloxy)ethyl 2-[4-(4-trifluoromethylphenoxy)phenoxy]propionate |
| 12 | 4-(4-Trifluoromethyl-2-chlorophenoxy)phenol sodium salt | 2-Benzyloxyethyl 2-chloropropionate | 2-Benzyloxyethyl 2-[4-(4-trifluoromethyl-2-chlorophenoxy)phenoxy]propionate |
| 13 | 4-(4-Bromo-2-chlorophenoxy)-phenol sodium salt | 2-Benzyloxyethyl 2-chloropropionate | 2-Benzyloxyethyl 2-[4-(4-bromo-2-chlorophenoxy)phenoxy]propionate |
| 14 | 4-(2-Chloro-4-cyano-phenoxy)phenol sodium salt | 2-Benzyloxyethyl 2-chloropropionate | 2-Benzyloxyethyl 2-[4-(2-chloro-4-cyanophenoxy)phenoxy]propionate |
| 15 | 4-(2,6-Dichloro-4-trifluoromethylphenoxy)phenol sodium salt | 2-Benzyloxyethyl 2-chloropropionate | 2-Benzyloxyethyl 2-[4-(2,6-dichloro-4-trifluoromethylphenoxy)phenoxy]propionate |
| 16 | 4-(3,5-Dichloro-2-pyridyloxy)phenol sodium salt | 1-Methyl-2-α-methyl-benzyloxyethyl 2-chloropropionate | 1-Methyl-2-α-methylbenzyloxyethyl 2-[4-(3,5-dichloro-2-pyridyloxy)phenoxy]propionate |
| 17 | 4-(3,5-Dichloro-2-pyridyloxy)phenol sodium SOH | 3-(4-Fluorobenzyloxy)-propyl 2-bromopropionate | 3-(4-Fluorobenzyloxy)propyl 2-[4-(3,5-dichloro-2-pyridyloxy)phenoxy]propionate |
| 18 | 4-(3,5-Dichloro-2-pyridyloxy)phenol sodium salt | 2-(3-Chlorobenzyloxy)-ethyl 2-chloropropionate | 2-(3-Chlorobenzyloxy)ethyl 2-[4-(3,5-dichloro-2-pyridyloxy)phenoxy]propionate |
| 19 | 4-(3,5-Dichloro-2-pyridyloxy)phenol sodium salt | 2-(4-Methylbenzyloxy)-ethyl 2-chloropropionate | 2-(4-Methylbenzyloxy)ethyl 2-[4-(3,5-dichloro-2-pyridyloxy)phenoxy]propionate |
| 20 | 2-Benzyloxyethanol | 2-[4-(5-Trifluoromethyl-2-pyridyloxy)phenoxy]-propionyl chloride | 2-Benzyloxyethyl 2-[4-(5-trifluoromethyl-2-pyridyloxy)phenoxy]propionate/m.p. 44–47° C. |
| 21 | 2-(2-Fluorobenzyloxy)-ethanol | 2-[4-(5-Trifluoromethyl-2-pyridyloxy)phenoxy]-propionyl chloride | 2-(2-Fluorobenzyloxy)ethyl 2-[4-(5-trifluoromethyl-2-pyridyloxy)phenoxy]propionate/m.p. 46–48.5° C. |
| 22 | 2-(4-Chlorobenzyloxy)-ethanol | 2-[4-(5-Trifluoromethyl-2-pyridyloxy)phenoxy]-propionyl chloride | 2-(4-Chlorobenzyloxy)ethyl 2-[4-(5-trifluoromethyl-2-pyridyloxy)phenoxy]propionate/$n_D^{20}$ 1.5350 |
| 23 | 2-(4-Methoxybenzyloxy)-ethanol | 2-[4-(5-trifluoromethyl-2-pyridyloxy)phenoxy]-propionyl bromide | 2-(4-Methoxybenzyloxy)ethyl 2-[4-(5-trifluoromethyl-2-pyridyloxy)phenoxy]propionate/$n_D^{20}$ 1.5335 |
| 24 | 1-Benzyloxy-2-propanol | 2-[4-(5-Trifluoromethyl-2-pyridyloxy)phenoxy]-propionyl bromide | 1-Methyl-2-benzyloxyethyl 2-[4-(5-trifluoromethyl-2-pyridyloxy)phenoxy]propionate/$n_D^{20}$ 1.5224 |
| 25 | 3-Benzyloxypropanol | 2-[4-(5-Trifluoromethyl-2-pyridyloxy)phenoxy]-propionyl chloride | 3-Benzyloxypropyl 2-[4-(5-trifluoromethyl-2-pyridyloxy)phenoxy]propionate/$n_D^{20}$ 1.5245 |
| 26 | 2-Benzyloxyethanol | 2-[4-(3-Chloro-5-nitro-2-pyridyloxy)phenoxy]-propionyl bromide | 2-Benzyloxyethyl 2-[4-(3-chloro-5-nitro-2-pyridyloxy)phenoxy]propionate |
| 27 | 2-Benzyloxyethanol | 2-[4-(3-Chloro-5-trifluoromethyl-2-pyridyloxy)phenoxy]propionyl chloride | 2-Benzyloxyethyl 2-[4-(3-chloro-5-trifluoromethyl-2-pyridyloxy)phenoxy]propionate |
| 28 | 2-(2-Methoxybenzyloxy)-ethanol | 2-[4-(3,5-Dichloro-2-pyridyloxy)phenoxy]-propionyl chloride | 2-(2-Methoxybenzyloxy)ethyl 2-[4-(3,5-dichloro-2-pyridyloxy)phenoxy]propionate |

EXAMPLE 29

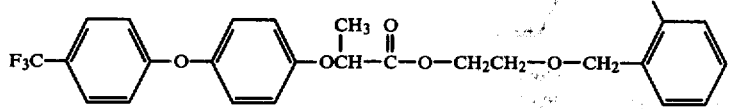

33.4 g of 2-(2-fluorobenzyloxy)ethyl-2-(4-hydroxyphenoxy)propionate was dissolved in 120 ml of dimethylformamide, 15.2 g of potassium carbonate were added thereto, then the mixture was heated at 95° C. for one hour with stirring. 27.1 g of 4-trifluoromethyl chlorobenzene were added to the solution which was then heated to 95° to 100° C. for five hours. After cooling the reaction solution to room temperature, it was poured into ice-water, then extracted with toluene. The toluene layer was washed successively with 1% strength by weight sodium hydroxide solution and water, and was dried and filtered. The toluene was distilled off under reduced pressure, and further volatile by-products were removed at 100° C./0.1 mmHg. The end product of 2-(2-fluorobenzyloxy)ethyl-2-[4-(4-trifluoromethylphenoxy)phenoxy]propionate was obtained in a yield of 20.7 g. ($n_D^{20}$ 1.5235)

EXAMPLE 30

31.6 g of 2-benzyloxyethyl-2-(4-hydroxyphenoxy)propionate were dissolved in 100 ml of dimethylsulfoxide, 15.2 g of potassium carbonate were added thereto, then the mixture was heated at 90° C. for one hour with stirring. 20.0 g of 2-chloro-5-trifluoromethylpyridine were added dropwise to this solution which was then maintained at 90° C. for a further two hours. After cooling the reaction solution to room temperature, it was poured into ice-water, then extracted with ether. The ether layer was dried and filtered, and the ether was distillated off. The end product of 2-benzyloxyethyl-2-[4-(5-trifluoromethyl-2-pyridyloxy)-phenoxy]propionate (a compound also produced in Example 20) was obtained in a yield of 41.0 g (m.p. 44°–47° C.).

EXAMPLES 31 TO 78

Compounds of the present invention shown in following Table 5 were obtained in substantially the same manner as in the foregoing Examples 1 to 30 (or, in the case of Example 40, as in foregoing Examples 1 to 28).

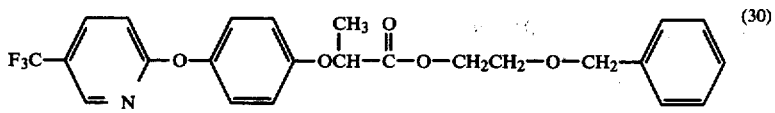

TABLE 5

| Example No. | Ar | R¹ | R² | n | $X_a$ | Physical constant |
|---|---|---|---|---|---|---|
| 31 | 2-CF₃-phenyl | H | H | 1 | H | $n_D^{20}$ 1.5322 |
| 32 | 4-F-phenyl | H | H | 1 | H | $n_D^{20}$ 1.5518 |
| 33 | 2,4-Cl₂-phenyl | H | H | 1 | H | $n_D^{20}$ 1.5696 |
| 34 | 4-O₂N-phenyl | H | H | 1 | H | $n_D^{20}$ 1.5805 |

TABLE 5-continued

[Structure: Ar—O—⌬—O—CH(CH₃)—C(=O)—O—CH(R¹)—(CH₂)ₙ—O—CH(R²)—⌬—Xₐ]

| Example No. | Ar | R¹ | R² | n | Xₐ | Physical constant |
|---|---|---|---|---|---|---|
| 35 | 5-Cl, 2-CF₃-phenyl | H | H | 1 | H | $n_D^{20}$ 1.5397 |
| 36 | 4-F₃C, 2-NO₂-phenyl | H | H | 1 | H | $n_D^{20}$ 1.5450 |
| 37 | 4-F₃C-phenyl | H | H | 2 | H | $n_D^{20}$ 1.5268 |
| 38 | 4-F₃C-phenyl | —CH₃ | H | 1 | H | $n_D^{20}$ 1.5260 |
| 39 | 4-F₃C-phenyl | H | —CH₃ | 1 | H | $n_D^{20}$ 1.5266 |
| 40 | 4-F₃C-phenyl | H | H | 1 | 4-F | $n_D^{20}$ 1.5214 |
| 41 | 4-F₃C-phenyl | H | H | 1 | 2-Cl | $n_D^{20}$ 1.5360 |
| 42 | 4-F₃C, 2-NO₂-phenyl | H | H | 1 | 2-Cl | $n_D^{20}$ 1.5550 |
| 43 | 4-F₃C-phenyl | H | H | 1 | 4-Cl | $n_D^{20}$ 1.5360 |
| 44 | 2-CF₃-phenyl | H | H | 1 | 4-Cl | $n_D^{20}$ 1.5380 |
| 45 | 5-Cl, 2-CF₃-phenyl | H | H | 1 | 4-Cl | $n_D^{20}$ 1.5450 |

TABLE 5-continued $$Ar-O-\underset{}{\underset{}{\bigcirc}}-O-\overset{CH_3}{\underset{CH}{|}}-\overset{O}{\underset{}{\|}}-O-\overset{R^1}{\underset{CH}{|}}(CH_2)_n-O-\overset{R^2}{\underset{CH}{|}}-\underset{}{\bigcirc}-X_a$$

| Example No. | Ar | R¹ | R² | n | $X_a$ | Physical constant |
|---|---|---|---|---|---|---|
| 46 | 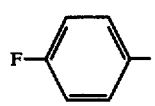 (4-F-C₆H₄) | H | H | 1 | 4-Cl | $n_D^{20}$ 1.5559 |
| 47 | 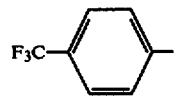 (4-F₃C-C₆H₄) | H | H | 1 | 2,4-Cl₂ | $n_D^{20}$ 1.5422 |
| 48 | 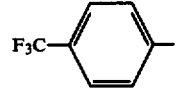 (4-F₃C-C₆H₄) | H | H | 1 | 3,4-Cl₂ | $n_D^{20}$ 1.5428 |
| 49 | 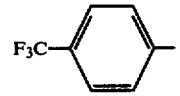 (4-F₃C-C₆H₄) | H | H | 1 | 2-CH₃ | $n_D^{20}$ 1.5305 |
| 50 | 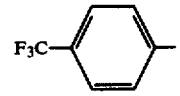 (4-F₃C-C₆H₄) | H | H | 1 | 3-NO₂ | $n_D^{20}$ 1.5436 |
| 51 | 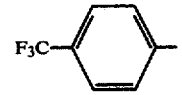 (4-F₃C-C₆H₄) | H | H | 1 | 4-OCH₃ | $n_D^{20}$ 1.5343 |
| 52 | 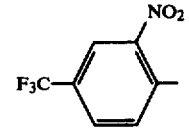 (2-NO₂-4-F₃C-C₆H₃) | H | H | 2 | H | $n_D^{20}$ 1.5440 |
| 53 | 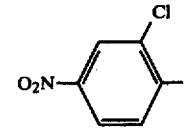 (2-Cl-4-O₂N-C₆H₃) | H | H | 1 | 4-Cl | $n_D^{20}$ 1.5875 |
| 54 | 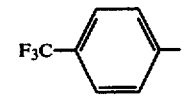 (4-F₃C-C₆H₄) | H | H | 1 | 4-Br | $n_D^{20}$ 1.5450 |
| 55 | 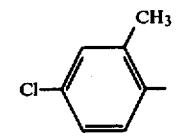 (2-CH₃-4-Cl-C₆H₃) | H | H | 1 | H | $n_D^{20}$ 1.5650 |
| 56 | 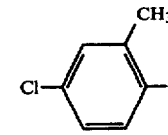 (2-CH₃-4-Cl-C₆H₃) | H | H | 1 | 2-Cl | $n_D^{20}$ 1.5718 |

TABLE 5-continued

Ar—O—⟨C₆H₄⟩—O—CH(CH₃)—C(O)—O—CH(R¹)—(CH₂)ₙ—O—CH(R²)—⟨C₆H₄⟩—Xₐ

| Example No. | Ar | R¹ | R² | n | Xₐ | Physical constant |
|---|---|---|---|---|---|---|
| 57 | 3,5-dichloropyridin-2-yl | H | H | 1 | H | m.p. 59–61° C. |
| 58 | 3,5-dichloropyridin-2-yl | H | —CH₃ | 1 | H | $n_D^{20}$ 1.5715 |
| 59 | 3,5-dichloropyridin-2-yl | H | H | 2 | H | $n_D^{20}$ 1.5721 |
| 60 | 5-nitropyridin-2-yl | H | H | 1 | H | oil |
| 61 | 5-nitropyridin-2-yl | H | H | 1 | 3-NO₂ | oil |
| 62 | 3,5-dichloropyridin-2-yl | H | H | 1 | 2-F | m.p. 54–57° C. |
| 63 | 3,5-dichloropyridin-2-yl | H | H | 1 | 2-Cl | m.p. 64–66° C. |
| 64 | 3,5-dichloropyridin-2-yl | H | H | 1 | 4-Cl | $n_D^{20}$ 1.5803 |
| 65 | 5-nitropyridin-2-yl | H | H | 1 | 4-Cl | oil |
| 66 | 3,5-dichloropyridin-2-yl | H | H | 1 | 3-NO₂ | $n_D^{20}$ 1.5845 |

TABLE 5-continued

Ar—O—⟨phenyl⟩—O—CH(CH₃)—C(O)—O—CH(R¹)(CH₂)ₙ—O—CH(R²)—⟨phenyl-Xₐ⟩

| Example No. | Ar | R¹ | R² | n | Xₐ | Physical constant |
|---|---|---|---|---|---|---|
| 67 | 3,5-dichloropyridin-2-yl | H | H | 1 | 2-CH₃ | m.p. 83–85° C. |
| 68 | 5-nitropyridin-2-yl | H | H | 1 | 2,4-Cl₂ | oil |
| 69 | 3,5-dichloropyridin-2-yl | H | H | 1 | 3,4-Cl₂ | $n_D^{20}$ 1.5900 |
| 70 | 3,5-dichloropyridin-2-yl | H | H | 1 | 2,6-Cl₂ | $n_D^{20}$ 1.5915 |
| 71 | 3,5-dichloropyridin-2-yl | H | H | 1 | 4-OCH₃ | $n_D^{20}$ 1.5735 |
| 72 | 3,5-dichloropyridin-2-yl | H | H | 1 | 4-Br | $n_D^{20}$ 1.5870 |
| 73 | 5-(trifluoromethyl)pyridin-2-yl | H | CH₃ | 1 | H | $n_D^{20}$ 1.5254 |
| 74 | 5-(trifluoromethyl)pyridin-2-yl | H | H | 1 | 2-CH₃ | $n_D^{20}$ 1.5273 |
| 75 | 5-(trifluoromethyl)pyridin-2-yl | H | H | 1 | 2-Cl | $n_D^{20}$ 1.5349 |
| 76 | 5-(trifluoromethyl)pyridin-2-yl | H | H | 1 | 4-Br | $n_D^{20}$ 1.5440 |
| 77 | 5-(trifluoromethyl)pyridin-2-yl | H | H | 1 | 3-NO₂ | $n_D^{20}$ 1.5428 |

TABLE 5-continued $$Ar-O-\underset{}{\underset{}{\bigcirc}}-O-\underset{CH_3}{\underset{|}{CH}}-\underset{O}{\underset{||}{C}}-O-\underset{R^1}{\underset{|}{CH}}(CH_2)_n-O-\underset{R^2}{\underset{|}{CH}}-\underset{}{\underset{}{\bigcirc}}-X_a$$

| Example No. | Ar | R¹ | R² | n | $X_a$ | Physical constant |
|---|---|---|---|---|---|---|
| 78 | F₃C—⟨pyridine⟩— | H | H | 1 | 2,4-Cl₂ | $n_D^{20}$ 1.5424 |

Processes for the preparation of the novel intermediate compounds of formulae (III) and (VII) according to the present invention are illustrated by the following Examples.

EXAMPLE 79

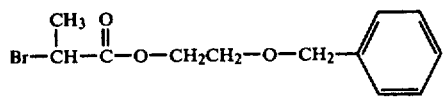

(a compound of formula (III)).

15.2 g of 2-benzyloxyethanol and 10.6 g of triethylamine were dissolved in 150 ml of toluene, and the solution was cooled to −5° C. A solution of 21.6 g of 2-bromopropionylbromide in 30 ml of toluene was added dropwise thereto at −5° to 0° C. with stirring. The reaction mixture was further maintained at room temperature for two hours. The mixture was then washed successively with 1% strength by weight sodium hydroxide solution and water, and the toluene solution was then dried and filtered. The toluene was distilled off under reduced pressure, and the end product of 2-benzyloxyethyl-2-bromopropionate was obtained in a yield of 26.7 g ($n_D^{20.5}$ 1.5182)

The intermediate compounds of the general formula (III) of this invention shown in Table 6 were produced in a manner similar to that described above:

TABLE 6

$$Z^1-\underset{CH_3}{\underset{|}{CH}}-\underset{O}{\underset{||}{C}}-O-\underset{R^1}{\underset{|}{CH}}(CH_2)_n-O-\underset{R^2}{\underset{|}{CH}}-\underset{}{\underset{}{\bigcirc}}-X_a \quad (III)$$

| Z¹ | R¹ | R² | n | $X_a$ | Physical constant |
|---|---|---|---|---|---|
| Br | H | H | 1 | 2-F | $n_D^{20}$ 1.5038 |
| Cl | H | H | 1 | 4-F | $n_D^{20}$ 1.5004 |
| Br | H | H | 1 | 4-F | $n_D^{20}$ 1.5040 |
| Br | H | H | 1 | 2-Cl | $n_D^{20.5}$ 1.5302 |
| Br | H | H | 1 | 4-Cl | $n_D^{20}$ 1.5289 |
| Cl | H | H | 1 | 4-Br | $n_D^{20.5}$ 1.5321 |
| Br | H | H | 1 | 4-Br | $n_D^{20.5}$ 1.5434 |
| Br | H | H | 1 | 2-CH₃ | $n_D^{20}$ 1.5186 |
| Br | H | H | 1 | 2-OCH₃ | $n_D^{20.5}$ 1.5260 |
| Br | H | H | 1 | 3-NO₂ | $n_D^{20}$ 1.5394 |
| Br | H | H | 1 | 2,4-Cl₂ | $n_D^{20}$ 1.5395 |
| Br | H | H | 1 | 3,4-Cl₂ | $n_D^{20}$ 1.5409 |
| Cl | H | H | 1 | 2,6-Cl₂ | $n_D^{20}$ 1.5412 |
| Br | CH₃ | H | 1 | H | $n_D^{20.5}$ 1.5100 |
| Br | H | CH₃ | 1 | H | $n_D^{20.5}$ 1.5116 |
| Br | H | H | 2 | H | $n_D^{20.5}$ 1.5130 |
| Br | H | H | 1 | 4-OCH₃ | $n_D^{20.5}$ 1.5250 |

EXAMPLE 80

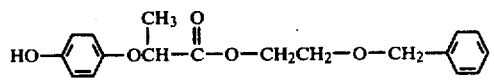

(a compound of formula (VII)).

12.1 g of hydroquinone were dissolved in 60 ml of dry dimethylformamide, 31.7 g of potassium carbonate were added thereto in a slow stream of nitrogen, and then the mixture was heated to 90° to 95° C. for one hour with stirring. The mixture was cooled to 60° C., and to it were added dropwise 28.7 g of 2-benzyloxyethyl-2-bromopropionate. The reaction mixture was heated at 90° C. for two hours. After cooling the reaction solution to room temperature, it was poured into ice-water and adjusted to pH7, then extracted with 100 ml of toluene. The toluene layer was dried and filtered, and then toluene was removed under reduced pressure. The colorless oily product of 2-benzyloxyethyl-2-(4-hydroxyphenoxy)propionate was obtained in a yield of 24.6 g. ($n_D^{21.5}$ 1.5390)

The intermediates compound of the general formula (VII) of this invention shown in Table 7 were produced in a manner similar to that described above:

TABLE 7

$$M-O-\underset{}{\underset{}{\bigcirc}}-O\underset{CH_3}{\underset{|}{CH}}-\underset{O}{\underset{||}{C}}-O-\underset{R^1}{\underset{|}{CH}}(CH_2)_n-O-\underset{R^2}{\underset{|}{CH}}-\underset{}{\underset{}{\bigcirc}}-X_a \quad (VII)$$

| M | R¹ | R² | n | $X_a$ | Physical constant |
|---|---|---|---|---|---|
| H | H | H | 1 | 2-F | $n_D^{21.5}$ 1.5260 |
| H | H | H | 1 | 4-Cl | $n_D^{21.5}$ 1.5473 |
| H | H | H | 1 | 3,4-Cl₂ | $n_D^{21.5}$ 1.5570 |
| H | CH₃ | H | 1 | H | $n_D^{20.5}$ 1.5321 |
| H | H | CH₃ | 1 | H | $n_D^{20.5}$ 1.5336 |
| H | H | H | 2 | H | $n_D^{21.5}$ 1.5344 |
| H | H | H | 1 | 4-OCH₃ | $n_D^{20.5}$ 1.5422 |

It will be understood that the specification and examples are illustrative but not limitative of the present invention and that other embodiments within the spirit and scope of the invention will suggest themselves to those skilled in the art.

What is claimed is:

1. A substituted phenoxypropionate of the formula

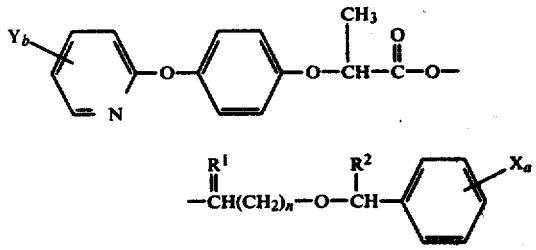

in which

R¹ and R² each independently is a hydrogen atom or a $C_1$ to $C_6$ alkyl group, X is a hydrogen or halogen atom, a nitro, $C_1$ to $C_6$ alkyl or $C_1$ to $C_6$ alkoxy group, a and n each independently is 1 or 2, Y is a trifluoromethyl group, a halogen atom or a nitro, cyano or $C_1$ to $C_6$ alkyl group, and b is 1 or 2.

2. Compound as claimed in claim 1 wherein R¹ is hydrogen.

3. Compound as claimed in claim 1 wherein R¹ is a $C_1$ to $C_6$ alkyl group.

4. Compound as claimed in claim 1 wherein R² is hydrogen.

5. Compound as claimed in claim 1 wherein R² is a $C_1$ to $C_6$ alkyl group.

6. Compound as claimed in claim 1 wherein X is hydrogen, halogen, nitro, $C_1$ to $C_4$ alkyl or $C_1$ to $C_4$ alkoxy.

7. Compound as claimed in claim 1, wherein R¹ and R² each independently is hydrogen, methyl, ethyl, n-propyl, isopropyl, n-butyl, sec-butyl or tert-butyl, X is a hydrogen atom, a fluorine, chlorine, bromine or iodine atom, a nitro, methyl, methoxy, ethyl, ethoxy, n-propyl, n-propoxyl, isopropyl, isopropoxy or n-, iso-, sec- or tert-butyl or -butoxy group, a and n each independently is 1 or 2, Y is a trifluoromethyl group, a fluorine, chlorine, bromine or iodine atom or a nitro, cyano, methyl, ethyl, propyl, isopropyl, n-, iso-, sec- or tert-butyl group and b is 1, 2 or 3.

8. Compound as claimed in claim 1, designated 2-(2-fluorobenzyloxy)ethyl 2-(4-(3,5-dichloropyridyloxy)-phenoxy)-propionate of the formula

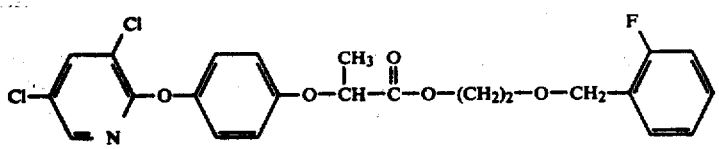

9. Compound as claimed in claim 1, designated 2-benzyloxyethyl 2-(4-(3,5-dichloropyridyloxy)-phenoxy)-propionate of the formula

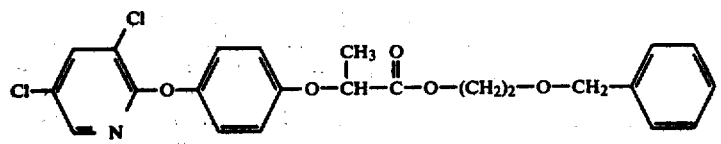

10. Compound as claimed in claim 1, designated 1-methyl-2-benzyloxyethyl 2-(4-(3,5-dichloropyridyloxy)-phenoxy)-propionate of the formula

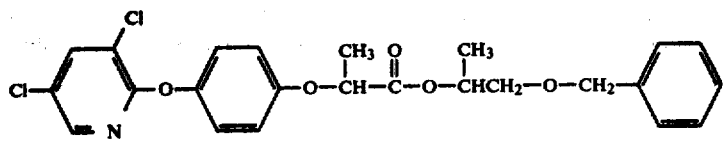

11. Compound as claimed in claim 1, designated 2-(4-chlorobenzyloxy)ethyl 2-(4-(3,5-dichloropyridyloxy)-phenoxy)-propionate of the formula

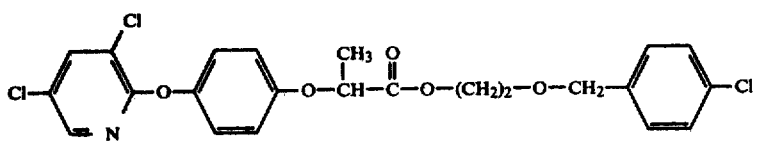

12. Compound as claimed in claim 1, designated 2-benzyloxyethyl 2-(4-(5-trifluoromethylpyridyloxy)-phenoxy)propionate of the formula

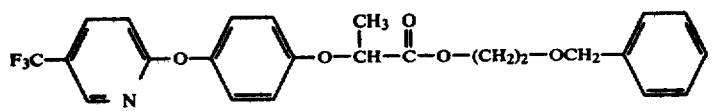

13. Compound as claimed in claim 1, designated 2-(2-fluorobenzyloxy)ethyl 2-(4-(5-trifluoromethyl pyridyloxy)phenoxy)propionate of the formula

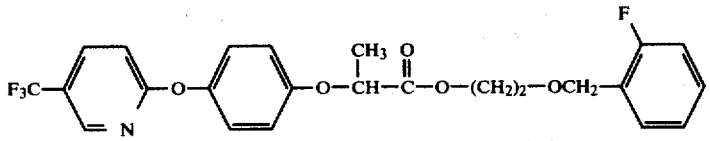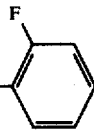

14. Compound as claimed in claim 1, designated 2-(4-chlorobenzyloxy)ethyl 2-(4-(5-trifluoromethyl pyridyloxy)phenoxy)propionate of the formula

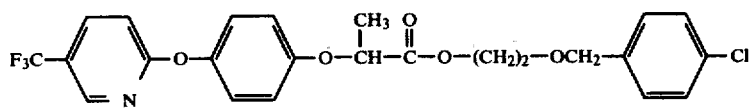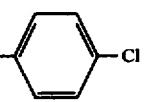

15. Compound as claimed in claim 1, designated 3-benzyloxypropyl 2-(4-(5-trifluoromethylpyridyloxy)-phenoxy)propionate of the formula

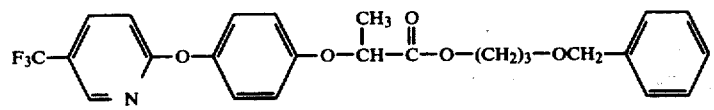

16. A herbicidal composition comprising an agriculturally acceptable carrier and, in herbicidally effective amount, a substituted phenoxypropionate as claimed in claim 1.

17. A herbicidal composition as claimed in claim 16, containing from 0.01 to 95% of the active compound, by weight.

18. A method of combating weeds which comprises applying to the weeds, or their habitat, a herbicidally effective amount of a substituted phenoxypropionate according to claim 1.

19. A method as claimed in claim 18, wherein said compound is applied at a dosage of 0.01 to 2 kg per hectare.

20. A method as claimed in claim 19, wherein said compound is applied at a dosage of 0.05 to 1 kg per hectare.

21. A method as claimed in claim 18, wherein said substituted phenoxypropionate compound is selected from 2-(2-fluorobenzyloxy)ethyl 2-(4-(3,5-dichloropyridyloxy)phenoxy)-propionate,
2-benzyloxyethyl 2-(4-(3,5-dichloropyridyloxy)-phenoxy)-propionate,
1-methyl-2-benzyloxyethyl 2-(4-(3,5-dichloropyridyloxy)phenoxy)-propionate,
2-(4-chlorobenzyloxy)ethyl 2-(4-(3,5-dichloropyridyloxy)phenoxy)-propionate,
2-benzyloxyethyl 2-(4-(5-trifluoromethylpyridyloxy)phenoxy)-propionate,
2-(2-fluorobenzyloxy)ethyl 2-(4-(5-trifluoromethylpyridyloxy)phenoxy)-propionate,
2-(4-chlorobenzyloxy)ethyl 2-(4-(5-trifluoromethylpyridyloxy)phenoxy)propionate, and
3-benzyloxypropyl 2-(4-(5-trifluoromethylpyridyloxy)phenoxy)propionate.

* * * * *